United States Patent
Lee et al.

(10) Patent No.: US 9,718,835 B2
(45) Date of Patent: Aug. 1, 2017

(54) 20(S)-SULFONYLAMIDINE DERIVATIVES OF CAMPTOTHECIN AND THE USE THEREOF AS A POTENT ANTITUMOR AGENT

(71) Applicant: China Medical University Hospital, Taichung (TW)

(72) Inventors: Kuo-Hsiung Lee, Chapel Hill, NC (US); Keduo Qian, Clarksburg, MD (US); Xiaoming Yang, Chapel Hill, NC (US); Masuo Goto, Chapel Hill, NC (US); Ying-Qian Liu, GanSu Province (CN); Yong-Long Zhao, Chengdu (CN); Liu Yang, GanSu Province (CN); Mei-Juan Wang, Lanzhou (CN); Zhi-Jun Zhang, Lanzhou (CN); Tian-Shung Wu, Tainan (TW); Che-Ming Teng, Taipei (TW); Chih-Ya Wang, Taipei (TW); Shiow-Lin Pan, Taipei (TW); Sheng-Chu Kuo, Taichung (TW); Hsin-Yi Hung, Taichung (TW); Ling-Chu Chang, Taichung (TW); Yang-Chang Wu, Kaohsiung (TW); Min-Tsang Hsieh, Taichung (TW); Chung Y. Hsu, Taichung (TW); Woei-Cherng Shyu, Taipei (TW); Chen-Huan Lin, Taichung (TW)

(73) Assignees: CHINA MEDICAL UNIVERSITY HOSPITAL, Taichung (TW); THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 15/025,296

(22) PCT Filed: Sep. 26, 2014

(86) PCT No.: PCT/US2014/057575
§ 371 (c)(1),
(2) Date: Mar. 28, 2016

(87) PCT Pub. No.: WO2015/048365
PCT Pub. Date: Apr. 2, 2015

(65) Prior Publication Data
US 2016/0229862 A1 Aug. 11, 2016

Related U.S. Application Data

(60) Provisional application No. 61/883,289, filed on Sep. 27, 2013.

(51) Int. Cl.
*C07D 491/12* (2006.01)
*C07D 471/04* (2006.01)
*C07D 491/22* (2006.01)
*C07F 9/6561* (2006.01)
*C07F 7/08* (2006.01)

(52) U.S. Cl.
CPC .......... *C07D 491/22* (2013.01); *C07F 7/0812* (2013.01); *C07F 9/6561* (2013.01)

(58) Field of Classification Search
CPC ........................... C07D 491/12; C07D 471/04
See application file for complete search history.

(56) References Cited

U.S. PATENT DOCUMENTS

2011/0300187 A1  12/2011  Yu et al.
2012/0165522 A1   6/2012  Cai et al.

FOREIGN PATENT DOCUMENTS

WO    2013/067449 A1    5/2013

OTHER PUBLICATIONS

International Search Report of corresponding International Application No. PCT/US2014/057575 mailed Dec. 29, 2014.
Gobis et al., "Synthesis, structure, and biological activity of novel heterocyclic sulfonyl-carboximidamides", Monatsh Chem, 2013, vol. 144, pp. 647-658.
Endo et al., "A water soluble prodrug of a novel camptothecin analog is efficacious against breast cancer resistance protein-expressing tumor xenografts", Cancer Chemother Pharmacol., 2010, vol. 65, pp. 363-371.

*Primary Examiner* — Bruck Kifle
(74) *Attorney, Agent, or Firm* — Bacon & Thomas, PLLC

(57) ABSTRACT

The present invention is related to novel 20-sulfonylamidine derivatives of camptothecin (1), method of synthesizing the same, and use thereof as an antitumor agent, for examples an antitumor agent for treating nasopharyngeal, lung, breast or prostate cancer.

26 Claims, 3 Drawing Sheets

20(S)-SULFONYLAMIDINE DERIVATIVES OF CAMPTOTHECIN AND THE USE THEREOF AS A POTENT ANTITUMOR AGENT

FIELD OF THE INVENTION

The present invention is related to novel 20-sulfonylamidine derivatives of camptothecin (1), methods of synthesizing, and using the same as an antitumor agent.

BACKGROUND

Camptothecin (CPT, 1, FIG. 1) is a naturally occurring alkaloid with remarkable antitumor effects.[1-3] Its antitumor activity has been ascribed to its ability to interfere with the catalytic cycle of DNA Topoisomerase I (Topo I) by stabilizing an irreversible drug-enzyme-DNA ternary complex and preventing religation of single-strand DNA breaks induced by Topo I.[4,5] Intensive synthetic medicinal chemistry efforts over the past decades have led to potent 1-derivatives, including is topotecan (2) and irinotecan (3), which are now used clinically to treat ovarian, small cell lung, and colon cancers. Also, several derivatives, such as gimatecan (4), CKD-602 (5), and BNP-1350 (6), are in various stages of preclinical or clinical development.[6-8] Although clinically used 1-derivatives remain a promising class of antitumor agents, their therapeutic use has been severely hindered by toxicity issues and delivery problems, due to poor water solubility, as well as instability of the active lactone form, due to preferential binding of the opened carboxylate to serum albumin.[9,10]

Several approaches, including the development of prodrugs (conjugates and polymer bound camptothecins), new formulations (liposomes or microparticulate carriers), and synthetic lipophilic camptothecins have been explored to improve the antitumor efficiency of the 1-family.[11-13] Most of these strategies aim to maintain the active closed-lactone form in the plasma compailinent. A free 20-hydroxyl group favors lactone ring-opening due to formation of intra-molecular hydrogen bonding,[14] while acylation of this group should stabilize the closed-lactone moiety.[15] Moreover, steric bulk in the introduced ester moiety can be desirable to impede hydrolysis of the ester bond by various enzymes, including carboxylesterases, thereby reducing the toxicity. Indeed, our own results,[16,17] as well as those of others with 20(S)—O-acyl esters,[18,19] 20(S)—O-carbonate linked tripeptide conjugates,[20] and 20(S)—O-linked glycoconjugates,[21] have supported the importance of esterified 1-derivatives for potent activity. Esterification of the 20-hydroxyl group also enhances plasma stability and augments in vivo antitumor activity compared with unmodified 1.

Amidines are well known as important pharmacophores[22-25] and widely used in bioactive chemicals and drug molecular design. Also, the introduction of a sulfonyl group into a bioactive functional fragment results in significant changes in the compound's bioactivity;[26,27] thus, sulfonylamidines may be useful structural motifs for optimization of bioactive molecules. Because this group is also quite bulky, it is likely to sterically prevent large enzymes from easily hydrolyzing a 20(S)—O-acyl ester of 1, which should also reduce the toxicity. In contrast, SN-38, the compound formed from the hydrolysis of 3, is quite toxic.[28] Given these considerations, we postulated that the introduction of a sulfonylamidine group at the 20-position of 1 could lead to improved efficacy and reduced toxicity as well as optimize the physicochemical properties of a new 1-related anticancer drug candidate. Therefore, in the present study, we incorporated the functional fragment sulfonylamidine into 1 at the C-20 position via a Cu-catalyzed one pot reaction[29] and synthesized a novel series of derivatives of 1 as potential antitumor agents.

SUMMARY OF THE INVENTION

The present invention is related to novel 20-sulfonylamidine derivatives of camptothecin (1), method of synthesizing the same, and use thereof as an antitumor agent.

A compound provided in the present invention has the following structure:

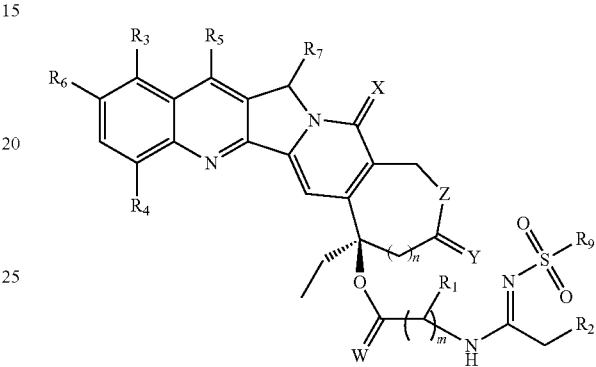

wherein
$R_1$ is H, C1-C6 alkyl, or phenyl C1-C3 alkyl;
$R_2$ is hydroxyl C1-C6 alkyl, $(CH_3)_k H_{3-k} Si$, phenyl, C1-C3 alkyl phenyl, C1-C3 alkoxyl phenyl, fluorophenyl, chlorophenyl, bromophenyl, $(CH_2)_j$—O—$(CH_2)_i$—$R_{11}$, wherein k is 0, 1, 2 or 3; j is 1-5; i is 0-5; and $R_{11}$ is

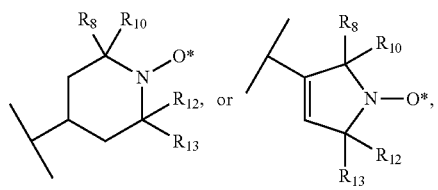

wherein $R_8$, $R_{10}$, $R_{12}$, and $R_{13}$ independently are H or C1-C6 alkyl;
$R_3$ is H, $NO_2$,

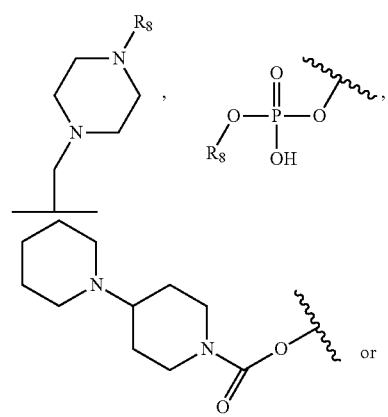

-continued

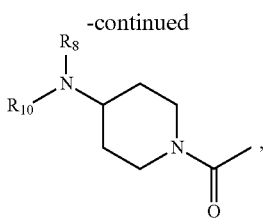

wherein $R_8$ and $R_{10}$ are defined as above;
$R_4$ is H or $NO_2$;
$R_5$ is H, C1-C6 alkyl,

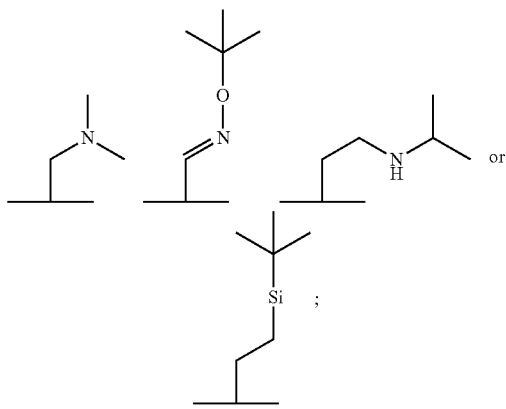

$R_6$ is H, OH, or

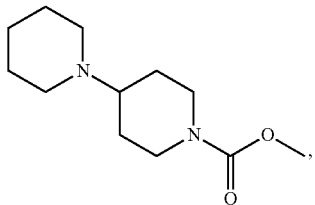 [SMILES: COC(=O)N1CCC(N2CCCCC2)CC1]

$R_7$ is H, C1-C6 alkyl or C1-C6 alkoxyl; and
$R_9$ is H, C1-C6 alkyl, phenyl, C1-C3 alkyl phenyl, C1-C3 alkoxyl phenyl, fluorophenyl, chlorophenyl, bromophenyl, pyridyl, naphthyl, furyl, thienyl, pyrrolyl,

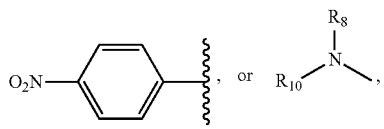

wherein $R_8$ and $R_{10}$ independently are H or C1-C6 alkyl;
n is 0-3;
m is 1-5;
X is O or S;
Y is O;
Z is O; and
W is O.

Preferably, $R_3$, $R_4$, $R_5$, $R_6$ and $R_7$ are all H, n is 0, m is 1, and X is O. More preferably, $R_9$ is C1-C6 alkyl, C1-C3 alkyl phenyl, C1-C3 alkoxyl phenyl, fluorophenyl, chlorophenyl, or

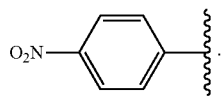

Most preferably, $R_2$ is hydroxyl C1-C6 alkyl, phenyl, C1-C3 alkoxyl phenyl, or $(CH_2)_j$—O—$(CH_2)_i$—$R_{11}$, wherein j is 1; i is 0 or 1; and
$R_{11}$ is

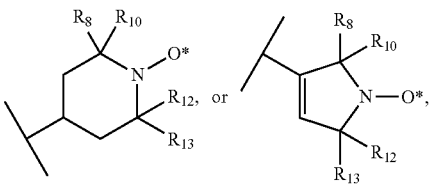

wherein $R_8$, $R_{10}$, $R_{12}$, and $R_{13}$ are all methyl. Further, $R_1$ preferably is H, C1-C6 alkyl, or phenylmethyl. More preferably, $R_2$ is p-methoxyphenyl. Alternatively, $R_2$ is $(CH_2)_j$—O—$(CH_2)_i$—$R_{11}$, wherein j is 1; i is 0 or 1; and $R_{11}$ is

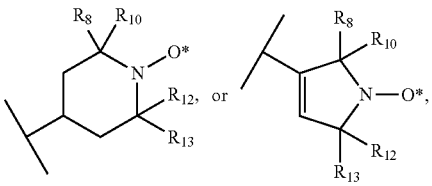

wherein $R_8$, $R_{10}$, $R_{12}$, and $R_{13}$ are all methyl.

Preferably, $R_2$ is p-methoxyphenyl or p-fluorophenyl, $R_1$ and $R_4$ are both H, $R_9$ is p-methylphenyl, n is 0, m is 1, and X is O. More preferably, $R_5$ is $CH_3CH_2$, $R_6$ is H or OH, $R_7$ is H, $R_2$ is p-methoxyphenyl, and $R_3$ is H. Alternatively, $R_5$ is $CH_3CH_2$, $R_6$ is H, $R_7$ is H, $R_2$ is p-methoxyphenyl, and $R_3$ is

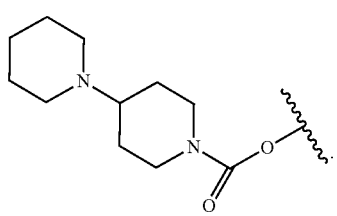 [SMILES: *OC(=O)N1CCC(N2CCCCC2)CC1]

When $R_2$ is p-methoxyphenyl or p-fluorophenyl, $R_1$ and $R_4$ are both H, $R_9$ is p-methylphenyl, n is 0, m is 1, and X is O, preferably i) $R_5$ and $R_7$ are both H, $R_6$ is OH, $R_2$ is p-methoxyphenyl, and $R_3$ is

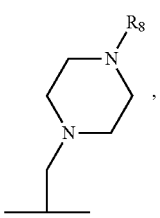

wherein $R_8$ is methyl; ii) $R_3$, $R_5$ and $R_6$ are all H, $R_7$ is methyl, $R_2$ is p-methoxyphenyl; or iii) $R_3$, $R_5$, $R_6$ and $R_7$ are all H, $R_2$ is p-fluorophenyl.

The use of claim 17, wherein the cancer is.

The present invention also provides a use of the aforesaid compound of the present invention in manufacturing a medicament for treating a cancer.

Preferably, the cancer is colon cancer, nasopharyngeal cancer, lung cancer, breast cancer, prostate cancer or ovary cancer.

The present invention further provides a method for treating a cancer comprising administering to a subject in need thereof an effective amount of the aforesaid compound of the present invention.

DETAILED DESCRIPTION OF THE INVENTION

Figure 1:
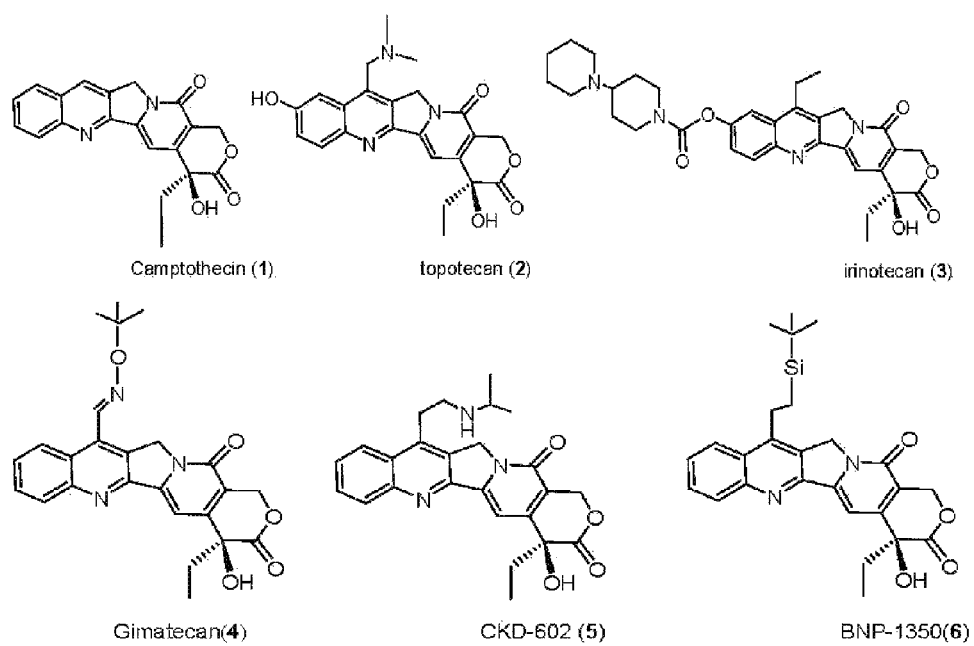
FIG. 1 shows structures of camptothecin (1), topotecan (2) and irinotecan (3), gimatecan (4), CKD-602 (5), and BNP-1350 (6).

We disclose herein the introduction of a sulfonylamidine group at the 20-position of 1 via a Cu-catalyzed one pot reaction to yield 9a-9l as potential antitumor agents.

Twelve novel 20-sulfonylamidine derivatives (9a-9l) of camptothecin (1) were synthesized via a Cu-catalyzed three-component reaction. They showed similar or superior cytotoxicity compared with irinotecan (3) against A-549, DU-145, KB, and multidrug-resistant (MDR) KBvin tumor cell lines. Compound 9a demonstrated better cytotoxicity against MDR cells compared with 1 and 3. Mechanistically, 9a induced significant DNA damage by selectively inhibiting Topoisomerase (Topo) I and activating the ATM/Chk related DNA damage-response pathway. In xenograft models, 9a demonstrated significant activity without overt adverse effects at 5 and 10 mg/kg, comparable to 3 at 100 mg/kg. Notably, 9a at 300 mg/kg (i.p.) showed no overt toxicity in contrast to 1 ($LD_{50}$ 56.2 mg/kg, i.p.) and 3 ($LD_{50}$ 177.5 mg/kg, i.p.). Intact 9a inhibited Topo I activity in a cell-free assay similarly to 1, confirming that 9a is a new class of Topo I inhibitor. 20-Sulfonylamidine 1-derivative 9a merits development as an anticancer clinical trial candidate.

Embodiment I

Chemistry.

As shown in Scheme 1, the 20-hydroxyl group of 1 was esterified to furnish N-Boc-amino acid derivatives (7) in suitable yields by a simple modification of the carbodiimide method using a combination of N,N'-diisopropyl carbodiimide (DIPC) and 4-dimethylaminopyridine (DMAP). The N-Boc group of 7 was removed with trifluoroacetic acid (TFA) in $CH_2Cl_2$ (1:1) to form the key intermediate TFA salts 8. Subsequently, we applied a highly efficient Cu-catalyzed three-component coupling reaction,[29] in which 8 was reacted with p-toluenesulfonyl azide and a wide range of alkynes to afford the desired compounds 9a-l in 35-58% yields. The structures of the target molecules were characterized from $^1$H-NMR, $^{13}$C-NMR, IR, and HR-MS data.

SCHEME 1

Synthesis of target compounds 9a-9l.

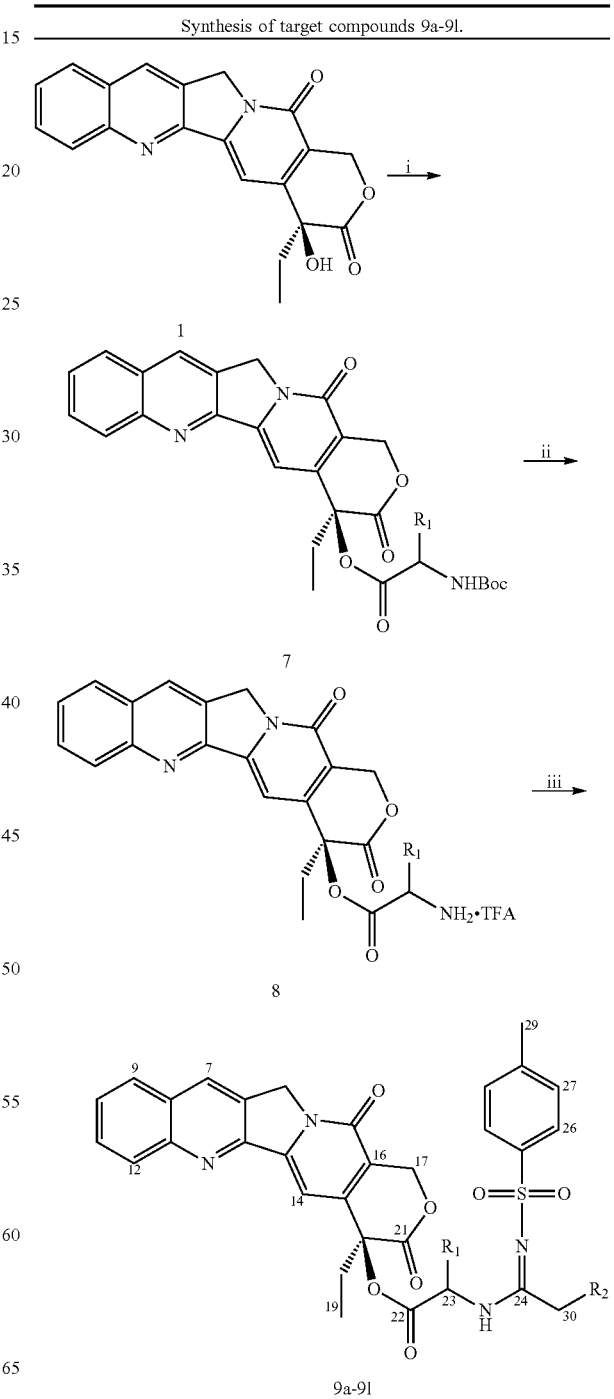

SCHEME 1-continued

| | $R_1$ | $R_2$ |
|---|---|---|
| 9a | H | p-MeO—Ph |
| 9b | H | Ph |
| 9c | $CH_3$ | p-MeO—Ph |
| 9d | $CH_3$ | Ph |
| 9e | $(CH_3)_2CH$ | p-MeO—Ph |
| 9f | $(CH_3)_2CH$ | Ph |
| 9g | $(CH_3)_2CHCH_2$ | p-MeO—Ph |
| 9h | $(CH_3)_2CHCH_2$ | Ph |
| 9i | $CH_3CH_2(CH_3)CH$ | p-MeO—Ph |
| 9j | $CH_3CH_2(CH_3)CH$ | Ph |
| 9k | $PhCH_2$ | p-MeO—Ph |
| 9l | $PhCH_2$ | $CH_2OH$ |

Reagents and conditions:
i DIPC/DMAP;
ii 50% $TFA-CH_2Cl_2$;
iii alkynes/CuI/$TsN_3$/$Et_3N$.

Antiproliferative Activity of New Compounds and Structure-Activity Relationship.

The 12 novel 1-derivatives 9a-l were evaluated for in vitro antiproliferative activity against four human tumor cell lines, KB (nasopharyngeal), A-549 (lung), DU-145 (prostate), and KBvin (MDR KB subline), by using a sulforhodamine B colorimetric assay with triplicate experiments.[30] Compounds 1 and 3 were used as controls. The screening results are shown in Table 1.

TABLE 1

In vitro cytotoxicity data for 9a-l against four tumor cell lines[a, b]

| | $IC_{50}$ (μM) | | | |
|---|---|---|---|---|
| compound | A-549 | DU-145 | KB | KBvin |
| 9a | 0.031 ± 0.0035 | 0.050 ± 0.0038 | 0.14 ± 0.018 | 0.026 ± 0.013 |
| 9b | 0.057 ± 0.0039 | 0.13 ± 0.011 | 0.18 ± 0.0008 | 0.10 ± 0.0073 |
| 9c | 0.089 ± 0.0083 | 0.14 ± 0.0059 | 0.91 ± 0.060 | 0.087 ± 0.0087 |
| 9d | 0.071 ± 0.0069 | 0.15 ± 0.022 | 0.22 ± 0.017 | 0.096 ± 0.0094 |
| 9e | 1.0 ± 0.11 | 1.7 ± 0.14 | 11 ± 0.48 | 1.5 ± 0.11 |
| 9f | 1.3 ± 0.12 | 2.0 ± 0.25 | 11 ± 0.28 | 2.2 ± 0.056 |
| 9g | 0.95 ± 0.018 | 1.6 ± 0.096 | 2.7 ± 0.0083 | 1.0 ± 0.13 |
| 9h | 0.89 ± 0.039 | 1.1 ± 0.016 | 4.4 ± 0.42 | 1.8 ± 0.030 |
| 9i | 1.2 ± 0.066 | 8.3 ± 0.14 | 9.6 ± 0.042 | 1.7 ± 0.16 |
| 9j | 6.5 ± 0.43 | 11 ± 0.75 | 11 ± 1.0 | 8.2 ± 0.61 |
| 9k | 0.12 ± 0.010 | 0.22 ± 0.025 | 0.85 ± 0.024 | 0.12 ± 0.0019 |
| 9l | 0.083 ± 0.010 | 0.20 ± 0.013 | 0.31 ± 0.021 | 0.14 ± 0.0081 |
| 1 | 0.016 ± 0.0005 | 0.029 ± 0.0025 | 0.037 ± 0.0031 | 0.12 ± 0.0091 |
| 3 | 9.5 ± 0.11 | 9.3 ± 0.61 | 9.8 ± 0.48 | >20 |

[a]Each assay was performed in triplicate with duplicated samples, and averaged $IC_{50}$ (μM) values are expressed with standard deviation (SD).
[b]A549 (lung carcinoma), DU-145 (hormone-insensitive prostate cancer), KB (originally isolated from epidermoid carcinoma of the nasopharynx), KBvin (vincristine-resistant KB subline).

All 12 new compounds (9a-l) exhibited significant in vitro cytotoxic activity against the four tested tumor cell lines, with $IC_{50}$ values ranging from 0.026 to 11 μM, indicating that both the $R^1$ and $R^2$ groups in the 20-sulfonylamidine side chain might influence the cytotoxic activity of the new 1-derivatives. The new compounds 9a-l (except 9a against KBvin) were less potent than 1; however, all of the new derivatives showed equivalent or superior cytotoxic activity compared with 3. Among the newly synthesized derivatives, 9a was the most potent compound against the four tested tumor cell lines. Interestingly, 9a also showed greater cytotoxic activity against KBvin ($IC_{50}$ 0.026 μM) compared with 1 and 3 ($IC_{50}$ 0.12 and >20 μM, respectively). The results also revealed that the A-549 cell line was more sensitive than the other three cell lines to these compounds, which is consistent with the clinical behavior of other 1-derivatives.[19]

Structure-activity relationship (SAR) correlations were also identified for these new 20-sulfonylamidine derivatives of 1. When the $R^2$ group was fixed as phenyl and the $R^1$ group in the sulfonylamidines was varied, hydrogen (9b) and methyl (9d) gave the best results compared with larger alkyl groups in 9f (isopropyl), 9h (isobutyl), and 9j (sec-butyl) Similar results were seen in the corresponding derivatives bearing a p-methoxyphenyl $R^2$ group. For example, against the A-549 cell line, the rank order of cytotoxic potency was 9a (H)>9c (methyl)>9g (isobutyl) ≥9e (isopropyl) ≥9i (sec-butyl). Therefore, small aliphatic chains appear to be the best $R^1$ substituents for greater cytotoxic potency. When the $R^1$ group was kept constant, and the $R^2$ group was changed from phenyl to p-methoxyphenyl, the cytotoxic activity often improved (for example, compare 9b to 9a, 9f to 9e, 9h to 9g, or 9j to 9i against KBvin). In addition, compound 9l bearing a hydroxymethyl $R^2$ group displayed comparable (DU-145, KB) or greater (A-549, KBvin) cytotoxic activity compared to 9k with a p-methoxyphenyl $R^2$ group. Compound 9k, which also has a benzyl $R^1$ group, generally exhibited intermediate potency between compounds with smaller (9a, 9c) and larger (9e, 9g, 9i) alkyl $R^1$ groups. These findings indicated that the cytotoxic profile of 1-derivatives may be sensitive to the size and electronic density of the substituents at C-20. Based on these in vitro results, compound 9a was selected for in vivo evaluation.

Mechanism of Action Studies on 9a.

Inhibition of Topo I activity by 9a in a cell-free system. A 1-delivative with an esterified 20-hydroxy group is expected to be activated by digestion with carboxylesterases. To determine whether intact 9a inhibits Topo I, a cell-free Topo I activity assay was employed using purified recombinant human Topo I. In this assay, supercoiled plasmid DNA is relaxed and nicked by recombinant Topo I. Thus, with the vehicle control or a test compound that has no inhibitory effect on Topo I activity, relaxed and nicked DNA is found. Compound 3, known to be a prodrug of 1, showed the same result, since it cannot be activated in this cell-free system as it is by carboxylesterases in the cell. In contrast, SN-38, a bioactive metabolite of 3, inhibited Topo I activity. Notably, we found that intact 9a inhibited Topo I activity in this cell-free assay similarly to 1. We authenticated the inhibitory effect of 9a against Topo I in a dose-dependent manner Thus, we confirmed that 9a is a new class of Topo I inhibitor.

Induction of Apoptosis by 9a in Human Tumor Cells.

Because A-549 human lung adenocarcinoma epithelial cells displayed higher sensitivity than the other tested cancer cell lines to 9a in the preliminary cytotoxicity profile, A-549 cells were used in our mechanistic study. Initially, we investigated morphological cellular changes. After exposure to 9a, A-549 cells showed apoptotic morphological features, including cell shrinkage and membrane blebbing. Apoptosis induction was further confirmed by double staining with FITC-annexin V and propidium iodide, showing that 9a treatment increased the percentage of apoptotic cells (annexin V positive cell population: vehicle versus 9a, 24 h, 1.1% versus 3.7%, $P<0.01$; 48 h, 2.0% versus 34.1%, $P<0.001$). Western blot analysis showed that cleaved caspases, the executors of apoptosis, were formed in response to 9a, including caspase-8, -9, and -3. PARP, a hallmark of apoptosis, was also activated by 9a. These data demonstrated that 9a inhibits A-549 cell growth through apoptosis induction.

Activation of DNA Damage Response Pathway by 9a.

The main effect of 1 is to bind to and stabilize the covalent Topo I-DNA complex, thus, induction of cell cycle delay in S phase, preventing DNA ligation and eventually leading to apoptosis.[31] Whether 9a activates the same pathway as 1 in A-549 cells was examined to demonstrate the mechanism of actions. First, we determined the effect of 9a on cell cycle distribution using flow cytometry analysis. As we expected, treatment with 9a for 24 h resulted in increased cell populations in S and sub-$G_1$ phases. A Topo I-mediated DNA cleavage assay was performed to examine whether 9a exhibits an inhibitory effect on Topo I activity in the cell. The results showed that 9a inhibited the relaxation of supercoiled DNA, which is similar to the effect of 1. However, both 9a and 1 failed to decatenate kineoplast DNA (kDNA), whereas etoposide, a known Topo II inhibitor, effectively blocked the decatenation of kDNA. Because it has been shown that 1-Topo I-DNA covalent complexes enhance the transcription-dependent degradation of Topo I via a 26S proteasome pathway,[32] the effects of 9a on the expression levels of Topo I and Topo II were investigated. Western blot analysis showed that 9a significantly inhibited protein levels of Topo I after 8 h treatment and slightly affected levels of Topo IIα and Topo IIβ after 24 h treatment. These results clearly demonstrated that 9a inhibited Topo I without interfering with Topo II activity. Compound 9a acts directly on Topo I and results in the accumulation of covalent Topo I-DNA complexes followed by proteasomal Topo I degradation, which is the same effect as 1 and contributes to 9a's cytotoxicity.

Compound 1 can induce DNA damage and activate ATM-Chk2 DNA damage-response pathway to trigger apoptotic pathways in cancer cells.[33] We found that ATM underwent phosphorylation at Ser1981 residue after 0.5 h treatment with 9a. Activation of ATM kinase was confirmed by detecting the phosphorylation of downstream effectors, Chk1, Chk2, and histone H2AX. Phosphorylation of H2AX at Ser139 residue (γH2AX) indicated that 9a caused DNA double strand break. P53 exerts a critical role on DNA-damage functions, including cell cycle regulation and apoptosis triggering.[34] The up-regulation and phosphorylation of p53 were greatly enhanced by 9a. P53 downstream apoptotic proteins such as PUMA and BAX were also predominantly increased by 9a. Furthermore, 9a up-regulated FADD, a component of death receptor-mediated extrinsic apoptosis, and down-regulated the pro-survival proteins Bcl-xL and Bcl-2 by preventing leakage of mitochondrial damage contents.

Taken together, compound 9a (YQL-9a) directly inhibits Topo I activity and depresses Topo I expression, which induces cell cycle delay at S phase as well as activation of DNA damage-response pathway, and subsequently activates apoptosis pathway. Our data support the superiority of 9a over the parent compound 1, suggesting that 9a is an excellent potential anticancer drug candidate. Therefore, we further investigated antitumor activity of 9a and toxicological evaluation in vivo.

Antitumor activity of 9a in vivo.

Figure 2:
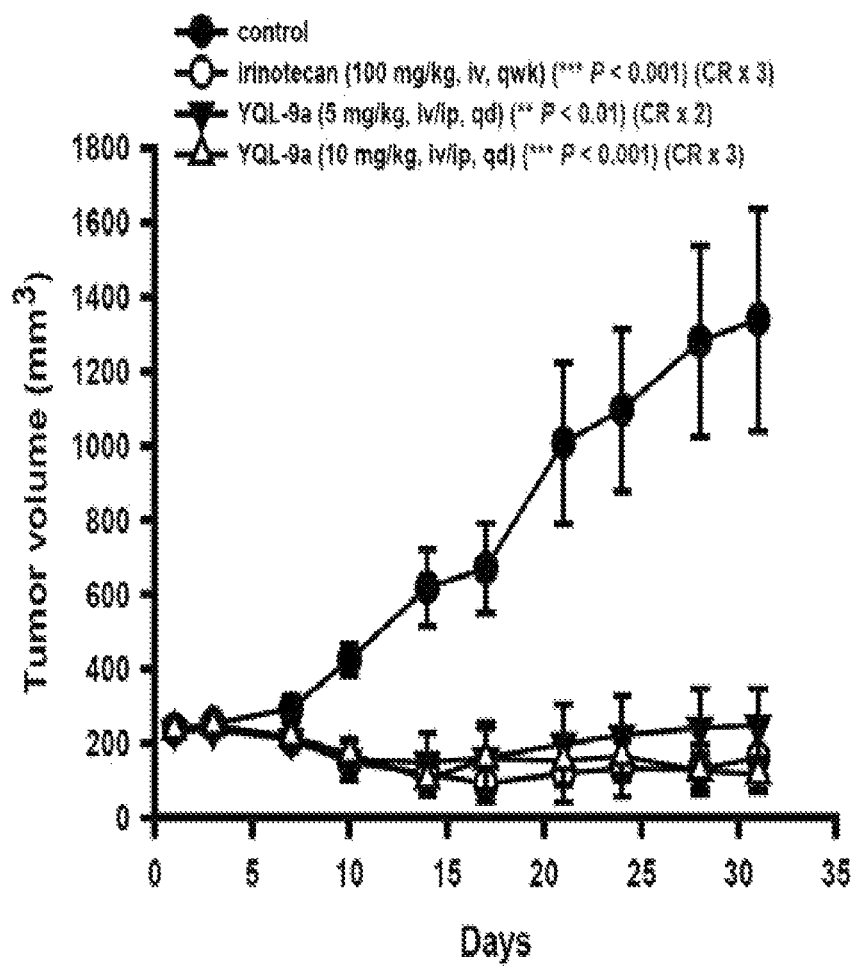
FIG. 2 shows anti-cancer activity of a compound, 9a, in human colorectal HCT116 cancer xenograft model, wherein the compound 9a is a novel compound synthesized in one of the preferred embodiments of the present invention.
Figure 3:
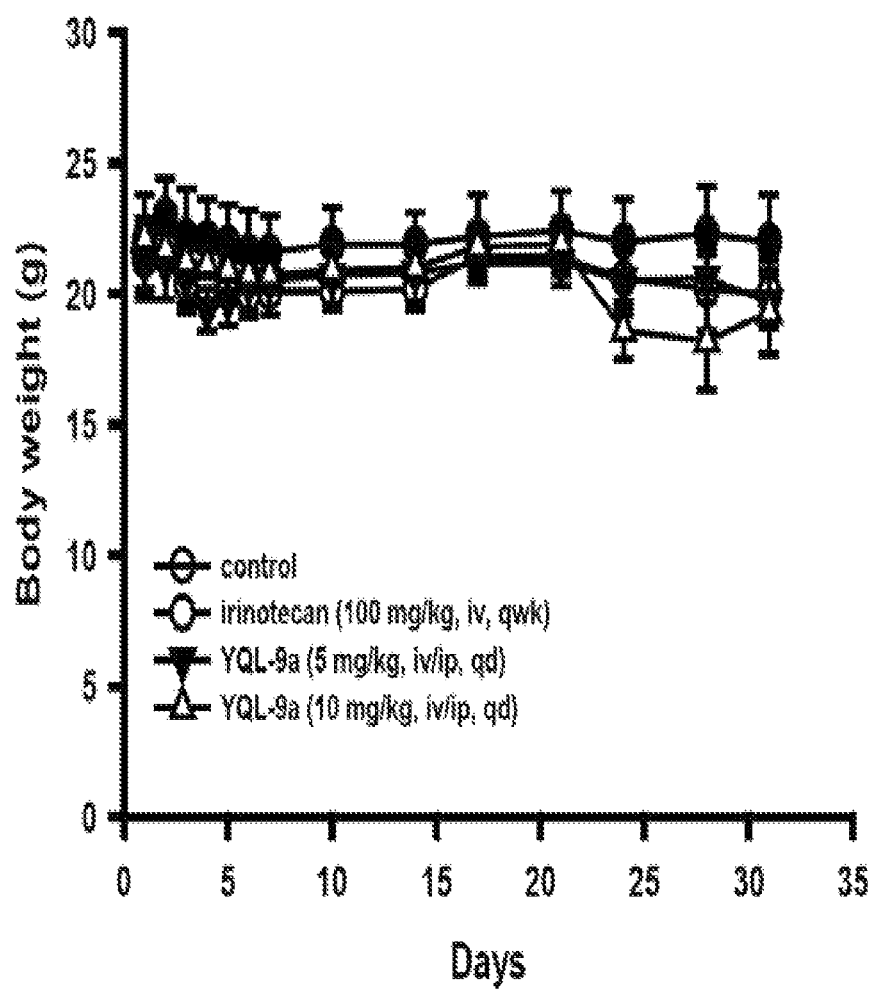
FIG. 3 shows 9a does not significantly affect the animal body weight.

Xenograft model antitumor assay using human colorectal adenocarcinoma cell line HCT116 was performed according to the regimen in Table 2. The 31-day study utilized four groups of mice (n=8) bearing established HCT116 xenograft with mean volumes of approximately 200 mm³ on day one. The tumor growth and animal body weight change for each treatment group were measured three times per week (FIGS. 2 and 3). Compound 9a was administered intravenously (i.v.) for 7 days and then intraperitoneally (i.p.) at 5 and 10 mg/kg once every day (QD) to the end. Two of eight and three of eight mice showed complete regression in the 5 mg/kg and 10 mg/kg dose groups, respectively. There were no significant changes in body weight at either dose. The experimental control using 3 also exhibited antitumor activity at a dose of 100 mg/kg once every week (QWK) ($P<0.001$) and three mice showed complete regression, supporting the accuracy of our in vivo evaluation. Based on the Student's t-test evaluation, 9a at 5 mg/kg ($P<0.01$) and 10 mg/kg ($P<0.001$) exhibited significant antitumor activity in vivo without overt signs of symptom and anaphylactic reaction.

TABLE 2

Study design of xenograft model antitumor assay.[a]

| | | Treatment Regimen | | |
| Group | n | Agent | mg/kg | Schedule |
| --- | --- | --- | --- | --- |
| 1 | 8 | 5% DMSO + 5% Cremophor | — | QD |
| 2 | 8 | Irinotecan | 100 | QWK |
| 3 | 8 | 9a | 5 | QD |
| 4 | 8 | 9a | 10 | QD |

[a]QD, once every day. QWK, once every week.

Toxicological Evaluation of 9a in Mice.

Acute toxicity of 9a in mouse was evaluated pathologically. Sixty 8-week-old male BALB/c mice were randomized into six groups (n=10) to receive 0 (vehicle only), 30, 100, 200, or 300 mg/kg of 9a i.p. on day zero. One group was kept without treatment as a normal control. All treated animals showed no anaphylactic responses, allergic reactions, or significant body weight loss, and were as healthy as the normal control animals, indicating significantly reduced toxicity compared with 1 ($LD_{50}$=56.2 mg/kg, i.p.) and 3 ($LD_{50}$=177.5 mg/kg, i.p.).[35] At the end of the experimental period, all animals were euthanized and tissues from liver, lung, kidney, and spleen were evaluated histopathologically according to the guidelines described by Shackelford et al.[36] as well as graded for symptomatic lesions. Histopathological evaluations included 1) glycogen deposition, inflammatory cell infiltration, and focal necrosis in liver, 2) regeneration of renal tubule, inflammatory cell infiltration, and chronic progressive nephropathy in kidney, and 3) inflammatory cell infiltration and adenoma in lung. Although a few microscopic lesions were observed in tissues from both 9a-treated and untreated mice, all lesions were considered spontaneous lesions and were not related to the 9a administration. Thus, 9a-treated animals showed no adverse effects according to hepatic, splenic, kidney and lung parameters. Thus, the animals apparently tolerated treatment with 300 mg/kg of 9a, portending an acceptable safety profile.

We postulate that the toxicological improvement against normal tissues might be associated with the introduction of a sulfonylamidine side chain at the 20-position of 1. Surprisingly, this modification does not disrupt the inhibitory effect against Topo I and may also prevent lactone ring-opening resulting in stabilization of the closed lactone moiety and contributing to better bioactivity of 1. Further studies including metabolic and pharmacokinetic evaluations, as well as introduction of a sulfonylamidine side chain at the C-7 position of 1, are currently underway to address this supposition.

In summary, a novel series of 20(S)-sulfonylamidine 1-derivatives were designed and synthesized with a key step being a Cu-catalyzed one pot reaction. All 12 derivatives showed comparable or superior cytotoxic activity compared with 3. Notably, compound 9a was as potent as 1 and far more potent than 3 against multidrug-resistant KBvin cells. The $IC_{50}$ values of the new derivatives ranged from 0.026 to 11 µM, indicating that the $R^1$ and $R^2$ groups in the 20-sulfonylamidine side chain could influence the cytotoxic activity of the new 1-derivatives greatly, leading to important SAR information. Also, 9a at 5 mg/kg and 10 mg/kg demonstrated significant antitumor activity in mice bearing established human HCT116 colorectal adenocarcinoma with no significant changes in body weight at all doses tested. In addition, two of eight and three of eight mice showed complete regression in the 5 mg/kg and 10 mg/kg dose groups, respectively. Histopathological evaluation of acute toxicity against liver, spleen, lung and kidney in mice showed no adverse effects of 9a treatment with 300 mg/kg. Based on these positive results, further development of 9a-related compounds as potential anticancer clinical trial candidates is definitely warranted.

Experimental Section

Chemistry General Information.

N-Boc-amino acids and TFA were purchased from GL Biochem (Shanghai) Company. DIPC and DMAP were purchased from Sigma Chemical Company (China). Other reagents and solvents were purchased from commercial sources and were used as received. The starting 1 was isolated from the Chinese medicinal plant C. acuminata, and was purified before being used (>98% is pure). Analytical thin-layer chromatography (TLC) and preparative thin-layer chromatography (PTLC) were performed with silica gel plates using silica gel 60 GF254 (Qingdao Haiyang Chemical Co., Ltd.). Melting points were taken on a Kofler melting point apparatus and are uncorrected. IR spectra were obtained on NIC-5DX spectrophotometer. MS analyses were performed on ZAB-HS and Bruker Daltonics APEXII49e instruments. NMR spectra were recorded on a Bruker AM-400 spectrometer at 400 MHz using TMS as reference (Bruker Company, USA). The purity of all tested compounds was determined by HPLC (Agilent Technologies 1100 series) equipped with a C-18 bounded-phase column (Eclipse Plus C18, 5 µM particle size, 4.6 mm×250 mm) A gradient elution was performed with MeOH and water as a mobile phase and was monitored at 254 nm. All tested compounds were >95% pure.

Synthesis of Key Intermediates 7 and 8.

The appropriate N-Boc-amino acid (3.13 mmol) was dissolved in 200 mL of anhydrous $CH_2Cl_2$ at rt. To this solution, DIPC (0.5 mL, 3.13 mmol), DMAP (3.13 mmol), and 1 (3.13 mmol) were added at 0° C.[16] The reaction mixture was allowed to warm to rt and left for 16 h. The solution was then washed with 0.1 N HCl, dried, and evaporated under reduced pressure to yield a white solid, which was recrystallized from MeOH to give a N-Boc-amino acid 1 ester derivative (7) in 56-87% yield. Subsequently, this intermediate (7, 1 mmol) was dissolved in a mixture of $CH_2Cl_2$ (10 mL) and TFA (10 mL) and stirred at rt for 1 h. Solvent was removed and the remaining solid was recrystallized from $CH_2Cl_2$ and diethyl ether to give the corresponding TFA salt (8) in 57-82% yield.

General Synthetic Procedure for Compounds 9a-9l.

Triethylamine (1.2 mmol) was added slowly to a suspension of the TFA salt 8 (0.5 mmol) in $CH_2Cl_2$ (35 mL), and this mixture was stirred for 10 min until a clear solution was obtained. Under an $N_2$ atmosphere, alkyne (0.5 mmol), p-toluenesulfonyl azide (0.6 mmol), and CuI (0.05 mmol) were added. The reaction mixture was stirred for 2-6 h at rt. After the reaction was completed, as monitored by TLC, the reaction mixture was diluted by adding $CH_2Cl_2$ (4 mL) and aqueous $NH_4Cl$ solution (6 mL). The mixture was stirred for an additional 30 min and two layers were separated. The aqueous layer was extracted with $CH_2Cl_2$ (3 mL×3). The combined organic layers were dried over $MgSO_4$, filtered, and concentrated in vacuo. The crude residue was purified by flash column chromatography on Si gel using $CHCl_3$-MeOH (10:1~20:1) as eluent to give 9a-9l.

Compound 9a.

Yield 52%; m.p. 129-131° C.; $t_R$-HPLC, 3.59 min (95.4%); IR (KBr) ν $cm^{-1}$: 3376, 3285, 2932, 1753, 1663, 1612, 1510, 1455, 1401, 1277, 1249, 1144, 1089, 1053, 892, 789, 688, 553; $^1H$ NMR (CDCl$_3$, 400 MHz) δ: 8.39 (s, 1H, C7-H), 8.24 (d, 1H, J=8.8 Hz, C9-H), 7.94 (d, 1H, J=8.0 Hz, C12-H), 7.85 (t, 1H, J=7.6 Hz, C11-H), 7.82 (d, 2H, J=8.0 Hz, Ts-H), 7.68 (t, 1H, C10-H), 7.32 (s, 1H, C14-H), 7.24 (d, 2H, J=8.0 Hz, Ts-H), 7.04 (d, 2H, J=8.4 Hz, -PhOCH$_3$), 6.83 (d, 2H, J=8.8 Hz, -PhOCH$_3$), 5.52 (ABq, 2H, J=17.2, C17-H), 5.26 (s, 2H, C5-H), 4.17-4.31 (m, 4H, C23, 30-H), 3.73 (s, 3H, -PhOCH$_3$), 2.39 (s, 3H, Ts-CH$_3$), 2.11-2.21 (m, 2H, C18-H), 0.91 (m, 3H, C19-H); $^{13}C$ NMR (100 MHz, CDCl$_3$) δ: 167.6, 167.1, 166.8, 159.4, 157.1, 152.2, 148.9, 146.7, 144.8, 131.3, 131.2, 130.8, 129.7, 129.2, 128.4, 128.2, 126.5, 142.4, 140.2, 120.1, 114.9, 95.6, 76.7, 67.2, 55.2, 50.0, 43.3, 38.5, 31.8, 21.5, 7.5; HRMS calcd for $C_{38}H_{34}N_4O_8S$: 729.1990 [M+Na]$^+$, found: 729.2002 [M+Na]$^+$.

Compound 9b.

Yield 54%; m.p. 132-134° C.; $t_R$-HPLC, 3.33 min (100%); IR (KBr) ν $cm^{-1}$: 3394, 3339, 3061, 2973, 2926, 1753, 1663, 1614, 1557, 1498, 1453, 1401, 1278, 1232, 1145, 1089, 1054, 985, 813; $^1H$ NMR (CDCl$_3$, 400 MHz) δ: 8.39 (s, 1H, C7-H), 8.24 (d, 1H, J=8.8 Hz, C9-H), 7.94 (d, 1H, J=8.0 Hz, C12-H), 7.82-7.86 (m, 3H, C11-H, Ts-H), 7.68 (t, 1H, C10-H), 7.33 (s, 1H, C14-H), 7.28-7.32 (m, 3H, Ph-H), 7.23 (d, 2H, J=8.0 Hz, Ts-H), 7.18 (d, 2H, J=8.0 Hz, Ph-H), 5.51 (ABq, 2H, J=17.2 Hz, C17-H), 5.26 (s, 2H, C5-H), 4.20-4.31 (m, 4H, C23, 30-H), 2.39 (s, 3H, Ts-CH$_3$), 2.11-2.22 (m, 2H, C18-H), 0.91 (m, 3H, C19-H); $^{13}C$ NMR (100 MHz, CDCl$_3$) δ 167.6, 166.8, 166.5, 157.2, 152.2, 148.9, 146.4, 144.8, 132.3, 131.2, 130.8, 130.1, 129.7, 129.5, 128.3, 126.5, 142.4, 140.2, 120.2, 95.6, 76.2, 67.2, 50.0, 43.3, 39.3, 31.7, 21.5, 7.5; HRMS calcd for $C_{37}H_{32}N_4O_7S$: 677.2064 [M+Na]$^+$, found: 677.2051 [M+Na]$^+$.

Compound 9c.

Yield 55%; m.p. 112-114° C.; $t_R$-HPLC, 2.92 min (96.9%); IR (KBr) ν cm$^{-1}$: 3371, 3261, 2931, 1751, 1662, 1611, 1548, 1402, 1277, 1249, 1144, 1085, 814, 759, 689; $^1$H NMR (CDCl$_3$, 400 MHz) δ 8.38 (s, 1H, C7-H), 8.26 (d, 1H, J=8.8 Hz, C9-H), 7.93 (d, 1H, J=8.0 Hz, C12-H), 7.80-7.83 (m, 3H, C11-H, Ts-H), 7.67 (t, 1H, C10-H), 7.36 (s, 1H, C14-H), 7.22 (d, 2H, J=8.0 Hz, Ts-H), 7.02 (d, J=8.8 Hz, -PhOCH$_3$), 6.81 (d, 2H, J=8.8 Hz, -PhOCH$_3$), 5.50 (ABq, 2H, J=17.2 Hz, C17-H), 5.26 (s, 2H, C5-H), 4.86 (m, 1H, C23-H), 4.23 (s, 2H, C30-H), 3.74 (s, 3H, -PhOCH$_3$), 2.39 (s, 3H, Ts-CH$_3$), 2.11-2.21 (m, 2H, C18-H), 1.47 (m, 3H, L-alanine-CH$_3$), 0.91 (m, 3H, C19-H); $^{13}$C NMR (100 MHz, CDCl$_3$) δ 170.8, 166.8, 166.3, 159.4, 157.2, 152.1, 148.9, 146.6, 144.7, 131.4, 131.1, 130.7, 130.5, 129.8, 129.5, 129.1, 128.4, 128.2, 128.0, 126.4, 124.3, 142.2, 140.3, 120.8, 114.8, 95.5, 67.2, 55.2, 50.0, 49.7, 38.6, 31.7, 21.5, 17.4, 7.5; HRMS calcd for $C_{39}H_{36}N_4O_8S$: 743.2146 [M+Na]$^+$, found 743.2157[M+Na]$^+$.

Compound 9d.

Yield 57%, 108-110° C.; $t_R$-HPLC, 3.55 min (100%); IR (KBr) ν cm$^{-1}$: 3395, 3311, 2979, 1755, 1667, 1619, 1541, 1402, 1277, 1231, 1143, 1085, 1058, 813, 755, 702; $^1$H NMR (CDCl$_3$, 400 MHz) δ 8.39 (s, 1H, C7-H), 8.22 (d, 1H, J=8.4 Hz, C9-H), 7.94 (d, 1H, J=8.0 Hz, C12-H), 7.80-7.89 (m, 3H, C11-H, Ts-H), 7.69 (t, 1H, C10-H), 7.38-7.41 (m, 2H, Ph-H), 7.36 (s, 1H, C14-H), 7.30-7.33 (m, 3H, Ph-H), 7.25 (d, 2H, J=8.0 Hz, Ts-H), 5.51 (ABq, 2H, J=17.2 Hz, C17-H), 5.25 (s, 2H, C5-H), 4.82 (m, 1H, C-23H), 4.33 (s, 2H, C30-H), 2.40 (s, 3H, Ts-CH$_3$), 2.11-2.21 (m, 2H, C18-H), 1.44 (d, 3H, L-alanine-CH$_3$), 0.89 (m, 3H, C19-H); $^{13}$C NMR (100 MHz, CDCl$_3$) δ 170.0, 166.7, 165.7, 157.2, 152.2, 148.9, 146.7, 144.6, 132.6, 131.1, 130.7, 130.2, 129.8, 129.5, 129.4, 129.2, 128.4, 128.2, 128.1, 126.4, 142.2, 140.2, 120.2, 95.3, 67.2, 50.0, 49.9, 39.5, 31.7, 21.5, 17.3, 7.5; HRMS calcd for $C_{38}H_{34}N_4O_7S$: 691.2221[M+H]$^+$, found: 691.2206 [M+H]$^+$.

Compound 9e.

Yield 55%; m.p. 118-120° C.; $t_R$-HPLC, 4.40 min (95.2%); IR (KBr) ν cm$^{-1}$: 3392, 3259, 2931, 1749, 1665, 1615, 1541, 1511, 1401, 1277, 1249, 1142, 1086, 812, 689, 553; $^1$H NMR (CDCl$_3$, 400 MHz) δ 8.38 (s, 1H, C7-H), 8.20 (d, 1H, J=8.8 Hz, C9-H), 7.94 (d, 1H, J=8.0 Hz, C12-H), 7.82 (t, 1H, C11-H), 7.72 (d, 2H, J=8.4 Hz, Ts-H), 7.66 (t, 1H, C10-H), 7.42 (d, 2H, J=8.4 Hz, -PhOCH$_3$), 7.36 (s, 1H, C14-H), 7.17 (d, 2H, J=8.0 Hz, Ts-H), 7.04 (d, 2H, J=8.8 Hz, -PhOCH$_3$), 5.51 (ABq, 2H, J=17.6 Hz, C17-H), 5.26 (s, 2H, C5-H), 4.61 (m, 1H, C23-H), 4.33 (s, 2H, C30-H), 3.80 (s, 3H, -PhOCH$_3$), 2.36 (s, 3H, Ts-CH$_3$), 2.18-2.20 (m, 3H, C18-H, L-valine-CH(CH$_3$)$_2$), 0.91 (m, 3H, C19-H), 0.74-0.89 (m, 6H, L-valine-CH(CH$_3$)$_2$); $^{13}$C NMR (100 MHz, CDCl$_3$) δ 168.4, 166.9, 166.6, 159.6, 157.2, 152.2, 148.9, 146.7, 144.1, 131.7, 131.0, 130.6, 129.8, 129.0, 128.4, 128.3, 128.1, 128.0, 126.2, 142.2, 140.2, 120.8, 115.1, 95.5, 76.3, 67.4, 59.2, 55.3, 50.1, 38.8, 31.7, 31.0, 21.4, 17.7, 7.5; HRMS calcd for $C_{41}H_{40}N_4O_8S$: 749.2640 [M+H]$^+$, found: 749.2648 [M+H]$^+$.

Compound 9f.

Yield 53%; m.p. 112-114° C.; $t_R$-HPLC, 4.53 min (95.1%); IR (KBr) ν cm$^{-1}$: 3399, 3263, 2964, 1752, 1666, 1620, 1561, 1534, 1455, 14399, 1277, 1256, 1141, 1085, 992, 806; $^1$H NMR (CDCl$_3$, 400 MHz) δ 8.38 (s, 1H, C7-H), 8.20 (d, 1H, J=8.8 Hz, C9-H), 7.93 (d, 1H, J=8.0 Hz, C12-H), 7.80 (t, 1H, C11-H), 7.73 (d, 2H, J=8.0 Hz, Ts-H), 7.66 (t, 1H, C10-H), 7.48-7.53 (m, 5H, Ph-H), 7.36 (s, 1H, C14-H), 7.16 (d, 2H, J=8.0 Hz, Ts-H), 5.51 (ABq, 2H, J=17.2 Hz, C17-H), 5.26 (s, 2H, C5-H), 4.60 (m, 1H, C23-H), 4.23 (s, 2H, C30-H), 2.35 (s, 3H, Ts-CH$_3$), 2.18-2.20 (m, 3H, C18-H, L-valine-CH(CH$_3$)$_2$), 0.91 (m, 3H, C19-H), 0.74-0.89 (m, 6H, L-valine-CH(CH$_3$)$_2$); $^{13}$C NMR (100 MHz, CDCl$_3$) δ 168.4, 166.6, 166.3, 157.2, 152.1, 148.9, 146.6, 144.1, 133.0, 131.0, 130.6, 130.4, 129.8, 129.3, 129.0, 128.4, 128.3, 128.0, 126.4, 140.3, 120.8, 95.5, 67.3, 59.1, 50.0, 39.6, 31.7, 31.0, 21.4, 17.5, 7.4; HRMS calcd for $C_{40}H_{38}N_4O_7S$: 719.2534 [M+H]$^+$, found: 719.2517 [M+H]$^+$.

Compound 9g.

Yield 54%; m.p. 130-132° C.; $t_R$-HPLC, 3.78 min (96.2%); IR (KBr) ν cm$^{-1}$: 3343, 3262, 2966, 2930, 1750, 1660, 1615, 1558, 1459, 1278, 1248, 1148, 1088, 814, 687; $^1$H NMR (CDCl$_3$, 400 MHz) δ 8.38 (s, 1H, C7-H), 8.22 (d, 1H, J=8.4 Hz, C12-H), 7.92 (d, 1H, J=8.0 Hz, C9-H), 7.82 (t, 1H, C11-H), 7.75 (d, 1H, J=8.0 Hz, C11-H), 7.65 (t, 1H, C10-H), 7.30 (d, 2H, J=8.0 Hz, Ts-H), 7.25 (s, 1H, C14-H), 7.02 (d, 2H, J=8.8 Hz, -PhOCH$_3$), 6.77 (d, 2H, J=8.8 Hz, -PhOCH$_3$), 5.32 (Abq, 2H, J=17.6 Hz, C17-H), 5.22 (s, 2H, C5-H), 4.24-4.29 (m, 3H, C23, C30-H), 3.74 (s, 3H, -PhOCH$_3$), 2.42 (s, 3H, Ts-CH$_3$), 2.33 (m, 3H, C18-H, L-leucine-CH$_2$CH(CH$_3$)$_2$), 1.20 (m, 1H, L-leucine-CH$_2$CH(CH$_3$)$_2$), 0.92 (t, 3H, C19-H), 0.85 (m, 6H, L-leucine-CH(CH$_3$)$_2$); $^{13}$C NMR (100 MHz, CDCl$_3$) δ: 170.6, 167.0, 159.3, 157.0, 152.1, 148.8, 146.6, 145.1, 143.3, 131.1, 131.0, 129.8, 129.6, 129.0, 128.3, 128.1, 128.0, 126.4, 126.3, 123.9, 142.1, 140.2, 119.9, 114.8, 96.2, 67.1, 55.2, 50.0, 42.1, 40.8, 38.6, 31.7, 24.8, 22.6, 21.5, 7.5; HRMS calcd for $C_{42}H_{42}N_4O_8S$: 763.2796 [M+H]$^+$, found: 763.2776 [M+H]$^+$.

Compound 9h.

Yield 48%; m.p. 125-127° C.; $t_R$-HPLC, 3.82 min (97.0%); IR (KBr) ν cm$^{-1}$: 3391, 3238, 2955, 1754, 1664, 1603, 1542, 1498, 1402, 1279, 1235, 1143, 1086, 1040, 810, 693; $^1$H NMR (CDCl$_3$, 400 MHz) δ 8.39 (s, 1H, C7-H), 8.29 (d, 1H, J=8.4 Hz, C9-H), 7.93 (d, 1H, J=8.0 Hz, C12-H), 7.83 (t, 1H, C11-H), 7.76 (d, 2H, J=8.4 Hz, Ts-H), 7.66 (t, 1H, C10-H), 7.36 (s, 1H, C14-H), 7.25-7.20 (m, 3H, Ts-H, Ph-H), 7.14-7.12 (m, 4H, Ph-H), 5.48 (ABq, 2H, J=17.2 Hz, C17-H), 5.26 (s, 2H, C5-H), 4.88 (m, 1H, C23-H), 4.03-4.36 (m, 2H, C30-H), 2.34 (s, 3H, Ts-CH$_3$), 2.11-2.21 (m, 2H, C18-H), 1.56-1.79 (m, 2H, L-leucine-CH$_2$CH(CH$_3$)$_2$), 1.48 (m, 1H, L-leucine-CH(CH$_3$)$_2$), 0.93 (m, 3H, C19-H), 0.83-0.93 (m, 6H, L-leucine-CH(CH$_3$)$_2$); $^{13}$C NMR (100 MHz, CDCl$_3$) δ: 170.6, 166.9, 166.3, 157.2, 152.1, 148.8, 146.6, 145.1, 132.5, 131.0, 130.0, 129.8, 129.6, 129.4, 129.0, 128.3, 128.1, 128.0, 126.4, 140.3, 120.1, 96.1, 67.2, 52.3, 50.0, 42.1, 40.8, 39.5, 31.7, 24.8, 22.8, 21.5, 7.5; HRMS calcd for $C_{41}H_{40}N_4O_7S$: 733.2690 [M+H]$^+$, found: 733.2670[M+H]$^+$.

Compound 9i.

Yield 58%; m.p. 127-129° C.; $t_R$-HPLC, 4.95 min (95.2%); IR(KBr) ν cm$^{-1}$: 3339, 3259, 2932, 1752, 1666, 1617, 1514, 1459, 1402, 1279, 1250, 1140, 1085, 1038, 896, 753, 677, 553; $^1$H NMR (CDCl$_3$, 400 MHz) δ 8.38 (s, 1H, C7-H), 8.19 (d, 1H, J=8.4 Hz, C9-H), 7.94 (d, 1H, J=8.4 Hz, C12-H), 7.81 (t, 1H, C11-H), 7.74 (d, 2H, J=8.0 Hz, Ts-H), 7.68 (t, 1H, J=8.0 Hz, C10-H), 7.40 (d, 2H, J=8.4 Hz, -PhOCH$_3$), 7.36 (s, 1H, C14-H), 7.17 (d, 2H, J=8.0 Hz, Ts-H), 7.03 (d, 2H, J=8.8 Hz, -PhOCH$_3$), 5.50 (ABq, 2H, J=17.2 Hz, C17-H), 5.26 (s, 2H, C5-H), 4.66 (m, 1H, C23-H), 4.33 (s, 2H, C30-H), 3.73 (s, 3H, -PhOCH$_3$), 2.39 (s, 3H, Ts-CH$_3$), 2.11-2.21 (m, 2H, C18-H), 1.92-1.98 (m, 1H, L-isoleucine-CH(CH$_3$)CH$_2$CH$_3$), 0.78-1.26 (m, 11H, C19-H, L-isoleucine-H); $^{13}$C NMR (100 MHz, CDCl$_3$) δ 168.2, 166.6, 166.4, 159.6, 157.2, 152.1, 148.9, 146.7, 144.8, 131.7, 131.0, 129.7, 129.6, 129.0, 128.3, 128.2, 128.0, 126.4, 124.6, 142.4, 140.2, 120.8, 115.1, 95.5, 67.5, 58.3, 55.3, 50.1, 42.1, 38.9, 37.9, 31.8, 24.9, 21.5, 15.0, 11.3, 7.4; HRMS calcd for C$_{42}$H$_{42}$N$_4$O$_8$S: 763.2796 [M+H]$^+$, found: 763.2788 [M+H]$^+$.

Compound 9j.

Yield 54%; m.p. 125-127° C.; $t_R$-HPLC, 3.72 min (96.2%); IR (KBr) ν cm$^{-1}$: 3339, 3258, 2966, 1751, 1666, 1619, 1539, 1454, 1401, 1280, 1258, 1142, 1085, 1051, 989, 693, 553; $^1$H NMR (CDCl$_3$, 400 MHz) δ 8.38 (s, 1H, C7-H), 8.20 (d, 1H, J=8.8 Hz, C12-H), 7.94 (d, 1H, J=8.0 Hz, C9-H), 7.81 (t, 1H, C11-H), 7.75 (d, 2H, J=8.0 Hz, Ts-H), 7.67 (t, 1H, C10-H), 7.50 (m, 4H, Ts, Ph-H), 7.37 (s, 1H, C14-H), 7.18 (d, 2H, J=8.0 Hz, Ph-H), 7.00 (s, 1H, Ph-H), 5.51 (ABq, 2H, J=17.6 Hz, C17-H), 5.26 (s, 2H, C5-H), 4.66 (m, 1H, C23-H), 4.40 (s, 2H, C30-H), 2.37 (s, 3H, Ts-CH$_3$), 1.90-2.23 (m, 3H, C18-H, L-isoleucine-CH(CH$_3$)CH$_2$CH$_3$), 1.14 (m, 2H, L-isoleucine-CH(CH$_3$)CH$_2$CH$_3$), 0.78-0.86 (m, 9H, C19-H, L-isoleucine-CH(CH$_3$)CH$_2$CH$_3$); $^{13}$C NMR (100 MHz, CDCl$_3$) δ: 168.2, 166.6, 166.0, 157.2, 152.2, 148.9, 146.7, 144.0, 133.0, 131.0, 130.6, 130.4, 129.8, 129.0, 128.4, 128.3, 128.2, 128.1, 126.2, 142.2, 140.3, 120.9, 95.5, 67.4, 50.1, 42.2, 39.7, 37.4, 31.8, 24.9, 21.4, 15.0, 11.3, 7.4; HRMS calcd for C$_{41}$H$_{40}$N$_4$O$_7$S: 733.2690 [M+H]$^+$, found: 733.2669 [M+H]$^+$.

Compound 9k.

Yield 52%; m.p. 102-104° C.; $t_R$-HPLC, 5.36 min (96.4%); IR (KBr) ν cm$^{-1}$: 3385, 3262, 2929, 1750, 1663, 1611, 1544, 1451, 1280, 1246, 1144, 1048, 812, 757, 693, 552; $^1$H NMR (CDCl$_3$, 400 MHz) δ 8.39 (s, 1H, C7-H), 8.22 (d, 1H, J=8.4 Hz, C9-H), 7.95 (d, 1H, J=8.0 Hz, C12-H), 7.82 (m, 3H, C11-H, Ts-H), 7.67 (t, 1H, C10-H), 7.36 (s, 1H, C14-H), 7.21 (d, 2H, J=8.0 Hz, Ts-H), 7.17-7.15 (m, 3H, L-phenylalanine-Ph), 7.10 (d, 2H, J=8.4 Hz, -PhOCH$_3$), 6.99-7.02 (m, 2H, L-phenylalanine-Ph), 6.89 (d, 2H, J=8.8 Hz, -PhOCH$_3$), 5.50 (ABq, 2H, J=17.2 Hz, C17-H), 5.26 (s, 2H, C5-H), 4.91 (m, 1H, C23-H), 4.23 (s, 2H, C30-H), 3.78 (s, 3H, -PhOCH$_3$), 3.12-3.06 (m, 2H, L-phenylalanine-√CH$_2$), 2.39 (s, 3H, Ts-√CH$_3$), 2.11-2.21 (m, 2H, C18-H), 0.81 (m, 3H, C19-H); $^{13}$C NMR (100 MHz, CDCl$_3$) δ 169.0, 166.7, 166.4, 159.4, 157.2, 152.2, 148.9, 146.2, 144.3, 134.8, 131.5, 131.0, 129.8, 129.4, 129.1, 128.6, 128.4, 128.2, 128.1, 127.2, 126.4, 124.0, 142.2, 140.3, 120.5, 114.9, 95.9, 67.2, 55.3, 54.9, 50.1, 38.7, 36.6, 32.0, 21.4, 7.4; HRMS calcd for C$_{45}$H$_{40}$N$_4$O$_8$S: 797.2640 [M+H]$^+$, found: 797.2661 [M+H]$^+$.

Compound 9l.

Yield 35%; m.p. 123-125° C.; $t_R$-HPLC, 3.20 min (100%); IR (KBr) ν cm$^{-1}$: 3419, 3269, 2925, 1751, 1644, 1601, 1540, 1401, 1277, 1236, 1139, 1087, 1050, 814, 758, 699, 552; $^1$H NMR (CDCl$_3$, 400 MHz) δ 8.45 (s, 1H, C7-H), 8.13 (d, 1H, J=8.4 Hz, C9-H), 7.97 (d, 1H, J=8.0 Hz, C12-H), 7.87 (t, 1H, C11-H), 7.71 (t, 1H, C10-H), 7.65 (d, 2H, J=8.4 Hz, Ts-H), 7.36 (s, 1H, C14-H), 7.22 (d, 2H, J=8.0 Hz, Ts-H), 7.17-7.20 (m, 5H, L-phenylalanine-Ph), 5.52 (ABq, 2H, J=17.2 Hz, C17-H), 5.26 (s, 2H, C5-H), 4.91 (m, 1H, C-23H), 4.11 (m, 2H, —CH$_2$OH), 3.14-3.23 (m, 2H, L-phenylalanine-CH$_2$), 2.39 (s, 3H, Ts-CH$_3$), 2.11-2.21 (m, 2H, C18-H), 0.91 (m, 3H, C19-H); $^{13}$C NMR (100 MHz, CDCl$_3$) δ: 167.7, 166.6, 166.5, 157.1, 152.1, 148.1, 145.8, 144.4, 135.1, 132.1, 131.3, 129.5, 129.4, 129.1, 129.0, 128.8, 128.5, 128.4, 128.3, 127.2, 126.4, 140.2, 121.0, 96.4, 67.2, 58.9, 56.1, 50.1, 37.5, 35.6, 32.0, 21.4, 7.5; HRMS calcd for C$_{39}$H$_{36}$N$_4$O$_8$S 743.2146 [M+Na]$^+$, found: 743.2158 [M+Na]$^+$.

Cell Lines and Cytotoxicity Assay.

The human tumor cell lines used in this manuscript were A-549 (lung carcinoma), MDA-MB-231 (triple-negative breast cancer), DU-145 (hormone-insensitive prostate cancer), KB (originally isolated from epidermoid carcinoma of the nasopharynx), KBvin (vincristine-resistant KB subline), and HCT116 (colorectal adenocarcinoma). These cell lines were obtained from the Lineberger Comprehensive Cancer Center (UNC-CH) or from ATCC (Manassas, Va.), except KBvin, which was a generous gift of Professor Y.-C. Cheng (Yale University). All cell lines were maintained and assayed in RPMI-1640 medium containing 2 mM L-glutamine and 25 mM HEPES (HyClone), supplemented with 10% heat-inactivated fetal bovine serum (HyClone), 100 μg/mL streptomycin, 100 IU/mL penicillin, and 0.25 μg/mL amphotericin B (Cellgro) in a humidified atmosphere containing 5% CO$_2$ in air. Compound stock solutions were prepared at 10 mM in DMSO and diluted with culture medium with the final DMSO concentration ≤0.01% (v/v), a concentration without effect on cell growth. The 4-6×10$^3$ cells/well were cultured for 72 h with various concentrations of test compounds in 96-well plate at 37° C. The antiproliferative activities of compounds were determined by sulforhodamine B assay according to the procedures developed and validated at NCI' and are expressed as IC$_{50}$ (μM) values, which reduced the cell number by 50% compared with vehicle control after 72 h of continuous treatment. Each assay was performed in triplicate with duplicated samples.

Morphological Observation.

Morphological changes of culture cells were observed under a phase contrast microscope and photographed with a digital camera (Nikon, Japan).

Apoptosis Assessment.

Apoptosis was detected by Annexin V-FITC/propidium iodide double staining kit (BD Biosciences). A-549 cells were treated with 9a for 24 h or 48 h. Cells were harvested by trypsinization and washed with ice-cold PBS. Cells were labeled with annexin V-FITC and propidium iodide for 15 min at room temperature in the dark. Labeled cells were analyzed by FACSCalibur flow cytometer (Becton Dickinson).

Cell Cycle Analysis.

A-549 cells were fixed with ice-cold 70% EtOH followed by propidium iodide staining Samples were analyzed by a flow cytometer for cell cycle determination. Population of each cell cycle phase was calculated based on the ploidy (<2N as sub-G1; 2N as G1; between 2N and 4N as S; 4N as G2/M), and evaluated statistically by Student's t-test (P<0.01).

Western Blot Analysis.

Cells were harvested in PBS containing proteinase inhibitors and phosphatase inhibitors, and sonicated. Whole cell lysates were separated by SDS-PAGE and transferred to Immobilon P membrane (EMD Millipore). The membrane was incubated with primary antibody followed by labeling with horseradish peroxidase (HRP)-conjugated secondary antibody (EMD Millipore). Chemilluminence substrate kit (EMD Millipore) was used for detection of membrane-bound HRP, and visualized by the Luminsence image analyzer, LAS4000 (Fuji Photo Film Co., Japan).

Antibodies.

Antibodies to caspase-3, caspase-8, caspase-9, PARP, phospho-ATM (Ser1981), ATM, phospho-ATR (Ser428), phospho-Chk1 (Ser345), phospho-Chk2 (Thr68), Chk2, phospho-H2AX (Ser139), and phospho-p53 (Ser15) were purchased from Cell Signaling Technology. Antibodies against ATM, ATR, Chk1, and PUMA were from Santa Cruz Biotechnology. Antibodies against Topo I, Topo IIα, Topo IIβ, p53, FADD, BAX, Bcl-xL, and Bcl-2 were from BD Biosciences. Antibody to β-actin was purchased from EMD Millipore.

Topoisomerase I Activity Assay in a Cell-Free System.

One unit of recombinant human Topoisomerase I enzyme (TopoGEN) was pre-incubated for 20 min at 37° C. with vehicle, 9a, 1, 3, or SN-38 in a final volume of 20 μL reaction buffer (10 mM Tris-HCl, pH 7.9, 1 mM EDTA, 150 mM NaCl, 0.1% BSA, 0.1 mM spermidine, 5% glycerol) was then incubated with 250 ng of supercoiled plasmid DNA for 20 min. The supercoiled, relaxed, or nicked DNA was separated by 1% agarose gel in 1×TAE (Tris-Acetate-EDTA) buffer. Ethidium bromide stained agarose gel was photographed using Gel Doc XR (Bio-Rad).

Topoisomerase I Activity Assay.

Topo I activity test was performed using an assay kit (TopoGEN) according to the manufacturer's instructions. Nuclear extracts from 9a-treated A-549 cells were incubated with supercoiled DNA (for Topo I) or catenated kDNA (for Topo II) for 30 min at 37° C. Reaction mixture was separated by is 1% agarose gel in 1×TAE buffer. The gel was stained with ethidium bromide and photographed using Gel Doc XR (Bio-Rad).

Xenograft Model Antitumor Assay.

Five- to six-week-old female nu/nu mice (National Laboratory Animal Center, Taiwan) were inoculated subcutaneously with 2×10$^6$ human colorectal adenocarcinoma HCT116 cells in flank. When the grafted tumor volume reached the average volume of 200 mm$^3$, mice were randomly divided into four groups (n=8). Treatment regimen is shown in Table 2. Vehicle control and compound 9a at 5 or 10 mg/kg were administered i.v. once a day (QD) for 7 days and then i.p. once a day to the end. As an experimental control group, 100 mg/kg of compound 3 was administered i.v. once a week (QWK) to the end. The length (L) and width (W) of graft was measured every 3 to 4 days to the end, and the tumor volume was calculated as LW$^2$/2. Results were evaluated statistically by Student's t-test. This study was approved by the Institutional Animal Care and Use Committee (IACUC) of the National Taiwan University (Taipei, Taiwan), and was performed according to the institutional guidelines.

Pathological Evaluation of In Vivo Toxicity.

Sixty 8-week-old male BALB/c mice (National Laboratory Animal Center, Taipei, Taiwan) were used to evaluate single-dose toxicity. Mice were randomly divided into six groups (n=10) and received a single i.p. injection of 9a at 0 (vehicle), 30, 100, 200 or 300 mg/kg on day 0. One group was untreated as normal control. Body weight was measured every three days for fifteen days. On the end of experimental period, all animals were euthanized by CO$_2$ and tissues from liver, lung, kidney and spleen were weighted (data not shown). Tissues were fixed with 10% formalin and embedded in paraffin. Sections 3-5 μm in thickness were prepared for histopathological examination. Hematoxylin and eosin (H&E) stained paraffin sections were evaluated histopathologically according to the guideline described by Shackelford et al.[36] and graded the symptomatic lesions. Degree of lesions were graded from one to five depending on severity as follows; [Nothing significant, 1=minimal (<1%), 2=slight (1-25%), 3=moderate (26-50%), 4=moderately severe (51-75%), 5=severe/high (76-100%)]. Statistically significant results (P<0.05) were is shown. This study was approved by the Institutional Animal Care and Use Committee (IACUC) of China Medical University (Taichung, Taiwan), and was performed according to the institutional guidelines.

ABBREVIATIONS

ATM, ataxia telangiectasia mutated; ATR, ataxia telangiectasia and Rad3-related; Chk, checkpoint kinase; CPT, camptothecin; DIPC, N,N'-diisopropyl carbodiimide; DMAP, 4-dimethylaminopyridine; FADD, Fas-associated protein with death domain; PUMA, p53 upregulated modulator of apoptosis; TFA, trifluoroacetic acid; Topo, topoisomerase Embodiments II Compounds 10a-10t were synthesized and identified by using procedures similar to those described in Embodiments I, which are shown in Table 3.

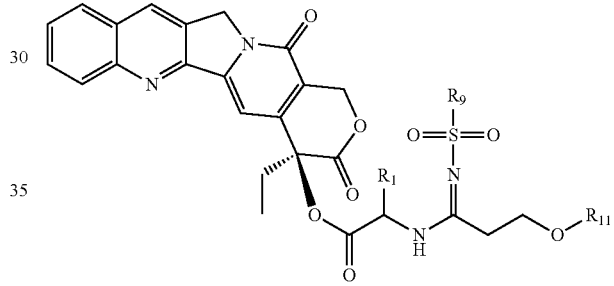

10a-10t

Triethylamine (1.2 mmol) was added slowly to a suspension of the various TFA salts 8 (0.5 mmol) in CH$_2$Cl$_2$ (35 mL), and this mixture was stirred for 10 min when a clear solution was obtained. Under an N$_2$ atmosphere, alkyne (0.5 mmol), sulfonylazide (0.6 mmol), and CuI (0.05 mmol) were added into this reaction mixture at room temperature. After the reaction was completed, as monitored by TLC, the reaction mixture was diluted by adding CH$_2$Cl$_2$ (4 mL) and aqueous NH$_4$Cl solution (6 mL). The mixture was stirred for an additional 30 min and two layers were separated. The aqueous layer was extracted with CH$_2$Cl$_2$ (3 mL×3). The combined organic layers were dried over MgSO$_4$, filtered, and concentrated in vacuo. The crude residue was purified by flash column chromatography with an appropriate eluting solvent system.

TABLE 3

| | R$_1$ | R$_9$ | R$_{11}$ |
|---|---|---|---|
| 10a | H | | |

TABLE 3-continued

| | $R_1$ | $R_9$ | $R_{11}$ |
|---|---|---|---|
| 10b | $CH_3$ | 4-methylphenyl | 2,2,6,6-tetramethyl-1-oxyl-piperidin-4-yl |
| 10c | $CH(CH_3)_2$ | 4-methylphenyl | 2,2,6,6-tetramethyl-1-oxyl-piperidin-4-yl |
| 10d | H | $CH_3$ | 2,2,6,6-tetramethyl-1-oxyl-piperidin-4-yl |
| 10e | H | $CH_3CH_2$ | 2,2,6,6-tetramethyl-1-oxyl-piperidin-4-yl |
| 10f | H | $CH_3(CH_3)_2$ | 2,2,6,6-tetramethyl-1-oxyl-piperidin-4-yl |
| 10g | H | 4-methoxyphenyl | 2,2,6,6-tetramethyl-1-oxyl-piperidin-4-yl |
| 10h | H | 4-chlorophenyl | 2,2,6,6-tetramethyl-1-oxyl-piperidin-4-yl |
| 10i | H | 4-fluorophenyl | 2,2,6,6-tetramethyl-1-oxyl-piperidin-4-yl |

TABLE 3-continued
| | $R_1$ | $R_9$ | $R_{11}$ |
|---|---|---|---|
| 10j | H | 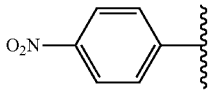 | 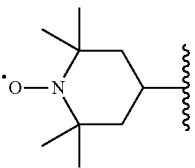 |
| 10k | $CH_2CH(CH_3)_2$ |  | 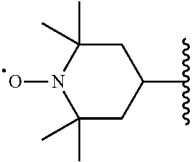 |
| 10l | $CH(CH_3)CH_2CH_3$ |  | 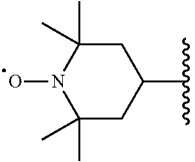 |
| 10m | $PhCH_2$ | 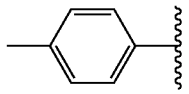 | 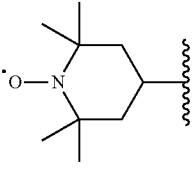 |
| 10n | H | 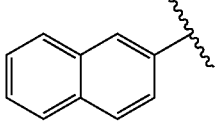 [SMILES: *c1ccc2ccccc2c1] | 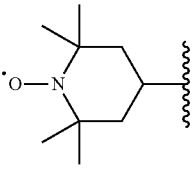 |
| 10o | H | 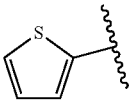 | 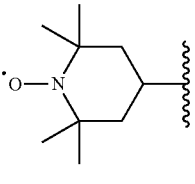 |
| 10p | H | 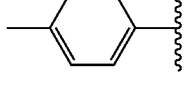 | 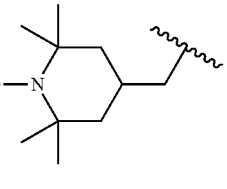 |
| 10q | H | $CH_3$ | 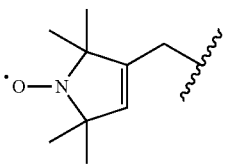 |

TABLE 3-continued

| | R₁ | R₉ | R₁₁ |
|---|---|---|---|
| 10r | H | 4-methylphenyl group | 2,2,5,5-tetramethyl-pyrroline-N-oxyl group |
| 10s | H | 4-methoxyphenyl (H₃CO-C₆H₄-) group | 2,2,5,5-tetramethyl-pyrroline-N-oxyl group |
| 10t | H | 4-fluorophenyl (F-C₆H₄-) group | 2,2,5,5-tetramethyl-pyrroline-N-oxyl group |

The In vitro cytotoxicity of compounds 10a-t against four human tumor cell lines are shown in Table 4.

TABLE 4

In vitro cytotoxicity of compounds 10a-t against four human tumor cell lines.[a]

| | IC$_{50}$(μM) (Average ± SD)[b] | | | |
|---|---|---|---|---|
| Compound | A-549 | MDA-MB-231 | KB | KBvin |
| 10a | 0.076 ± 0.026 | 0.45 ± 0.10 | 0.21 ± 0.016 | 0.11 ± 0.010 |
| 10b | 0.45 ± 0.0067 | 0.53 ± 0.0099 | 0.56 ± 0.0086 | 0.25 ± 0.080 |
| 10c | >1 | >1 | >1 | >1 |
| 10d | 0.059 ± 0.021 | 0.11 ± 0.024 | 0.071 ± 0.030 | 0.090 ± 0.037 |
| 10e | 0.055 ± 0.013 | 0.080 ± 0.0077 | 0.059 ± 0.0015 | 0.057 ± 0.014 |
| 10f | 0.062 ± 0.015 | 0.23 ± 0.12 | 0.075 ± 0.011 | 0.095 ± 0.0094 |
| 10g | 0.081 ± 0.010 | 0.27 ± 0.12 | 0.11 ± 0.0011 | 0.096 ± 0.0056 |
| 10h | 0.063 ± 0.015 | 0.19 ± 0.076 | 0.073 ± 0.0080 | 0.084 ± 0.013 |
| 10i | 0.086 ± 0.0065 | 0.27 ± 0.090 | 0.12 ± 0.028 | 0.10 ± 0.0035 |
| 10j | 0.058 ± 0.012 | 0.10 ± 0.0024 | 0.059 ± 0.020 | 0.072 ± 0.014 |
| 10k | 0.61 ± 0.0057 | 0.84 ± 0.0016 | 0.70 ± 0.021 | 0.74 ± 0.031 |
| 10l | >1 | >1 | >1 | >1 |
| 10m | 0.17 ± 0.087 | 0.50 ± 0.097 | 0.31 ± 0.18 | 0.10 ± 0.0016 |
| 10n | 0.48 ± 0.022 | 0.61 ± 0.0066 | 0.58 ± 0.013 | 0.33 ± 0.066 |
| 10o | 0.063 ± 0.0021 | 0.11 ± 0.010 | 0.063 ± 0.026 | 0.083 ± 0.022 |
| 10p | 0.062 ± 0.0038 | 0.091 ± 0.0025 | 0.080 ± 0.020 | 0.084 ± 0.011 |
| 10q | 0.0629 ± 0.0061 | 0.1027 ± 0.0027 | 0.0823 ± 0.0327 | 0.0834 ± 0.0207 |
| 10r | 0.074 ± 0.0054 | 0.12 ± 0.0029 | 0.091 ± 0.013 | 0.094 ± 0.0021 |
| 10s | 0.090 ± 0.0040 | 0.18 ± 0.0013 | 0.13 ± 0.038 | 0.15 ± 0.0059 |
| 10t | 0.077 ± 0.0006 | 0.14 ± 0.0033 | 0.12 ± 0.026 | 0.095 ± 0.0013 |
| 2 | 0.045 ± 0.0004 | 0.10 ± 0.0055 | 0.063 ± 0.0042 | 0.40 ± 0.021 |

[a]A549 (lung carcinoma), MDA-MB-231 (triple-negative breast cancer), KB (originally isolated from epidermoid carcinoma of the nasopharynx), KBvin (vincristine-resistant KB subline).
[b]Each assay was performed in triplicate with duplicated sample, and averaged IC$_{50}$ (μM) values were expressed with standard deviation (SD)

Compound 10a. Yield 70%; yellow orange solid; mp133-134° C.; IR (KBr) ν (cm$^{-1}$): 3432, 2978, 2939, 1753, 1664, 1618, 1560, 1449, 1402, 1385 (NO.), 1273, 1147, 1094, 881, 761, 669, 616, 556; Anal. Calcd for $C_{41}H_{46}N_5O_9S$: C, 62.74; H, 5.91; N, 8.92. Found: C, 62.70; H, 6.01; N, 8.87; EPR: $g_0$=2.0064, An=14.62Gs (triplet peak in 1×10$^{-4}$M, DMF); MS-ESI m/z: 785.3 [M+H]$^+$.

Compound 10b. Yield 67%; yellow orange solid; mp118-121° C.; IR (KBr) ν (cm$^{-1}$): 3433, 2977, 2938, 1752, 1664, 1618, 1545, 1458, 1403, 1384 (NO.), 1273, 1145, 1090, 881, 787, 724, 616, 555; Anal. Calcd for $C_{42}H_{48}N_5O_9S$: C, 63.14; H, 6.06; N, 8.77. Found: C, 63.10; H, 6.01; N, 8.90; EPR: $g_0$=2.0060, An=14.62Gs (triplet peak in 1×10$^{-4}$M, DMF); MS-ESI m/z: 800.2 [M+2H]$^+$.

Compound 10c. Yield 71%; yellow orange solid; mp128-130° C.; IR (KBr) ν (cm$^{-1}$): 3448, 2975, 2930, 2873, 1751, 1666, 1618, 1561, 1546, 1439, 1402, 1385 (NO.), 1272, 1145, 1091, 881, 670, 616, 555; Anal. Calcd for $C_{44}H_{52}N_5O_9S$: C, 63.90; H, 6.34; N, 8.47. Found: C, 64.03; H, 6.31; N, 8.56; EPR: $g_0$=2.0061, An=14.62Gs (triplet peak in 1×10$^{-4}$M, DMF); MS-ESI m/z: 828.3 [M+2H]$^+$.

Compound 10d. Yield 70%; yellow orange solid; mp125-127° C.; IR (KBr) ν (cm$^{-1}$): 3448, 2974, 2929, 1752, 1655, 1618, 1560, 1508, 1402, 1385 (NO.), 1272, 1122, 881, 788, 670, 617, 474; Anal. Calcd for $C_{35}H_{42}N_5O_9S$: C, 59.31; H, 5.97; N, 9.88. Found: C, 59.43; H, 6.01; N, 8.79; EPR: $g_0$=2.0066, An=14.62Gs (triplet peak in $1\times10^{-4}$M, DMF); MS-ESI m/z: 731.3 [M+Na]$^+$.

Compound 10e. Yield 64%; yellow orange solid; mp124-126° C.; IR (KBr) ν (cm$^{-1}$): 3431, 2974, 2929, 1753, 1655, 1618, 1561, 1508, 1439, 1403, 1384 (NO.), 1270, 1233, 1118, 881, 787, 758, 616, 475; Anal. Calcd for $C_{36}H_{44}N_5O_9S$: C, 59.82; H, 6.14; N, 9.69. Found: C, 59.73; H, 6.08; N, 9.58; EPR: $g_0$=2.0064, An=14.62Gs (triplet peak in $1\times10^{-4}$M, DMF); MS-ESI m/z: 745.4 [M+Na]$^+$.

Compound 10f. Yield 66%; yellow orange solid; mp123-125° C.; IR (KBr) ν (cm$^{-1}$): 3423, 2973, 2926, 2870, 1758, 1663, 1618, 1561, 1458, 1404, 1384 (NO.), 1267, 1234, 1181, 1119, 881, 788, 763, 724, 669, 616; Anal. Calcd for $C_{38}H_{48}N_5O_9S$: C, 60.78; H, 6.44; N, 9.33. Found: C, 60.89; H, 6.38; N, 9.50; EPR: $g_0$=2.0060, An=14.62Gs (triplet peak in $1\times10^{-4}$M, DMF); MS-ESI m/z: 773.4 [M+Na]$^+$.

Compound 10g. Yield 68%; yellow orange solid; mp142-144° C.; IR (KBr) ν (cm$^{-1}$): 3423, 2975, 2931, 1753, 1664, 1618, 1560, 1499, 1458, 1403, 1384 (NO.), 1257, 1146, 1094, 881, 854, 805, 762, 724, 696, 614, 555; Anal. Calcd for $C_{41}H_{46}N_5O_{10}S$: C, 61.49; H, 5.79; N, 8.74. Found: C, 61.54; H, 5.86; N, 8.67; EPR: $g_0$=2.0062, An=14.62Gs (triplet peak in $1\times10^{-4}$M, DMF); MS-ESI m/z: 823.2 [M+Na]$^+$.

Compound 10h. Yield 73%; yellow orange solid; mp144-146° C.; IR (KBr) ν (cm$^{-1}$): 3423, 2975, 2934, 1753, 1666, 1618, 1561, 1508, 1458, 1402, 1385 (NO.), 1272, 1234, 1149, 1095, 881, 762, 726, 618, 483; Anal. Calcd for $C_{40}H_{43}ClN_5O_9S$: C, 59.66; H, 5.38; N, 8.70. Found: C, 59.70; H, 5.45; N, 8.57; EPR: $g_0$=2.0064, An=14.62Gs (triplet peak in $1\times10^{-4}$M, DMF); MS-ESI m/z: 806.3 [M+2H]$^+$.

Compound 10i. Yield 64%; yellow orange solid; mp105-107° C.; IR (KBr) ν (cm$^{-1}$): 3422, 2975, 2930, 2871, 1753, 1663, 1593, 1560, 1496, 1458, 1403, 1383 (NO.), 1272, 1236, 1147, 1091, 1050, 880, 839, 764, 669, 616, 555; Anal. Calcd for $C_{40}H_{43}FN_5O_9S$: C, 60.90; H, 5.49; N, 8.88. Found: C, 61.01; H, 5.55; N, 8.49; EPR: $g_0$=2.0066, An=14.62Gs (triplet peak in $1\times10^{-4}$M, DMF); MS-ESI m/z: 790.3 [M+2H]$^+$.

Compound 10j. Yield 68%; yellow orange solid; mp135-137° C.; IR (KBr) ν (cm$^{-1}$): 3393, 2973, 2901, 1757, 1663, 1606, 1560, 1529, 1450, 1404, 1384 (NO.), 1351, 1223, 1150, 1081, 1050, 880, 747, 617, 464; Anal. Calcd for $C_{40}H_{43}N_6O_{11}S$: C, 58.89; H, 5.31; N, 10.30. Found: C, 58.94; H, 5.45; N, 10.25; EPR: $g_0$=2.0060, An=14.62Gs (triplet peak in $1\times10^{-4}$M, DMF); MS-ESI m/z: 817.4 [M+2H]$^+$.

Compound 10k. Yield 62%; yellow orange solid; mp120-122° C.; IR (KBr) ν (cm$^{-1}$): 3385, 2973, 2900, 1750, 1663, 1618, 1549, 1452, 1404, 1384 (NO.), 1272, 1234, 1146, 1087, 1050, 880, 814, 763, 689, 618, 556; Anal. Calcd for $C_{45}H_{54}N_5O_9S$: C, 64.27; H, 6.47; N, 8.33. Found: C, 64.38; H, 6.56; N, 8.21; EPR: $g_0$=2.0062, An=14.62Gs (triplet peak in $1\times10^{-4}$M, DMF); MS-ESI m/z: 842.4 [M+2H]$^+$.

Compound 10l. Yield 70%; yellow orange solid; mp122-124° C.; IR (KBr) ν (cm$^{-1}$): 3401, 2973, 2935, 2873, 1751, 1664, 1604, 1545, 1458, 1403, 1384 (NO.), 1273, 1147, 1091, 1051, 881, 815, 669, 617, 556; Anal. Calcd for $C_{45}H_{54}N_5O_9S$: C, 64.27; H, 6.47; N, 8.33. Found: C, 64.38; H, 6.56; N, 8.21; EPR: $g_0$=2.0064, An=14.62Gs (triplet peak in $1\times10^{-4}$M, DMF); MS-ESI m/z: 842.4 [M+2H]$^+$.

Compound 10m. Yield 68%; yellow orange solid; mp112-114° C.; IR (KBr) ν (cm$^{-1}$): 3402, 2974, 2901, 1751, 1655, 1618, 1560, 1544, 1450, 1405, 1384 (NO.), 1250, 1079, 1066, 1050, 881, 701, 617; Anal. Calcd for $C_{48}H_{52}N_5O_9S$: C, 65.89; H, 5.99; N, 8.00. Found: C, 65.98; H, 6.12; N, 8.06; EPR: $g_0$=2.0066, An=14.62Gs (triplet peak in $1\times10^{-4}$M, DMF); MS-ESI m/z: 876.4 [M+2H]$^+$.

Compound 10n. Yield 59%; yellow orange solid; mp141-143° C.; IR (KBr) ν (cm$^{-1}$): 3411, 2974, 2932, 1754, 1662, 1604, 1560, 1458, 1403, 1384 (NO.), 1272, 1236, 1127, 1082, 1050, 880, 787, 724, 688, 619, 555, 480; Anal. Calcd for $C_{44}H_{46}N_5O_9S$: C, 64.37; H, 5.65; N, 8.53. Found: C, 64.30; H, 5.54; N, 8.46; EPR: $g_0$=2.0062, An=14.62Gs (triplet peak in $1\times10^{-4}$M, DMF); MS-ESI m/z: 822.4 [M+2H]$^+$.

Compound 10o. Yield 67%; yellow orange solid; mp136-138° C.; IR (KBr) ν (cm$^{-1}$): 3423, 2975, 2938, 1753, 1663, 1617, 1560, 1458, 1404, 1384 (NO.), 1292, 1234, 1143, 1093, 1015, 881, 762, 724, 669, 618, 592; Anal. Calcd for $C_{38}H_{42}N_5O_9S_2$: C, 58.75; H, 5.45; N, 9.01. Found: C, 58.65; H, 5.38; N, 9.21; EPR: $g_0$=2.0066, An=14.62Gs (triplet peak in $1\times10^{-4}$M, DMF); MS-ESI m/z: 878.3 [M+2H]$^+$.

Compound 10p. Yield 75%; yellow orange solid; mp105-107° C.; IR (KBr) ν (cm$^{-1}$): 3423, 2974, 2928, 1756, 1663, 1601, 1560, 1457, 1403, 1384 (NO.), 1273, 1236, 1177, 1147, 1094, 1050, 920, 881, 818, 763, 695, 615, 556, 480; Anal. Calcd for $C_{42}H_{48}N_5O_9S$: C, 63.14; H, 6.06; N, 8.77. Found: C, 63.04; H, 6.19; N, 8.92; EPR: $g_0$=2.0060, An=14.62Gs (triplet peak in $1\times10^{-4}$M, DMF); MS-ESI m/z: 800.4 [M+2H]$^+$.

Compound 10q. Yield 65%; light yellow solid; mp121-123° C.; IR (KBr) ν (cm$^{-1}$): 3415, 2973, 2931, 2871, 1757, 1663, 1603, 1561, 1442, 1402, 1384 (NO.), 1256, 1190, 1120, 1084, 1049, 977, 881, 787, 724, 613, 562, 475; Anal. Calcd for $C_{35}H_{40}N_5O_9S$: C, 59.48; H, 5.70; N, 9.91. Found: C, 59.56; H, 5.63; N, 10.02; EPR: $g_0$=2.0058, An=14.76Gs (triplet peak in $1\times10^{-4}$M, DMF); MS-ESI m/z: 729.3 [M+Na]$^+$;

Compound 10r. Yield 61%; light yellow solid; mp110-112° C.; IR (KBr) ν (cm$^{-1}$): 3422, 2974, 2929, 1752, 1655, 1603, 1560, 1458, 1439, 1384 (NO.), 1273, 1147, 1093, 1050, 881, 724, 695, 616, 556; Anal. Calcd for $C_{41}H_{44}N_5O_9S$: C, 62.90; H, 5.66; N, 8.95. Found: C, 63.00; H, 5.53; N, 9.01; EPR: $g_0$=2.0055, An=14.76Gs (triplet peak in $1\times10^{-4}$M, DMF); MS-ESI m/z: 805.4 [M+Na]$^+$.

Compound 10s. Yield 70%; light yellow solid; mp120-122° C.; IR (KBr) ν (cm$^{-1}$): 3415, 2974, 2929, 1756, 1664, 1598, 1560, 1499, 1458, 1403, 1384 (NO.), 1258, 1146, 1094, 1051, 881, 836, 805, 725, 697, 614, 567; Anal. Calcd for $C_{41}H_{44}N_5O_{10}S$: C, 61.64; H, 5.55; N, 8.77. Found: C, 61.81; H, 5.42; N, 8.85; EPR: $g_0$=2.0058, An=14.76Gs (triplet peak in $1\times10^{-4}$M, DMF); MS-ESI m/z: 800.3 [M+2H]$^+$.

Compound 10t. Yield 69%; light yellow solid; mp103-105° C.; IR (KBr) ν (cm$^{-1}$): 3423, 2974, 2927, 1753, 1663, 1592, 1560, 1495, 1458, 1403, 1384 (NO.), 1279, 1234, 1186, 1148, 1091, 880, 839, 763, 724, 699, 613, 554, 481; Anal. Calcd for $C_{40}H_{41}FN_5O_9S$: C, 61.06; H, 5.25; N, 8.90. Found: C, 61.21; H, 5.15; N, 9.02; EPR: $g_0$=2.0055, An=14.76Gs (triplet peak in $1\times10^{-4}$M, DMF); MS-ESI m/z: 809.4 [M+Na]$^+$.

Embodiments III

More derivatives were synthesized and identified by using procedures similar to those described in Embodiments I, which are shown in Table 5.

The In vitro cytotoxicity of several compounds in Table 5 against four human tumor cell lines are shown in Table 6.

TABLE 5

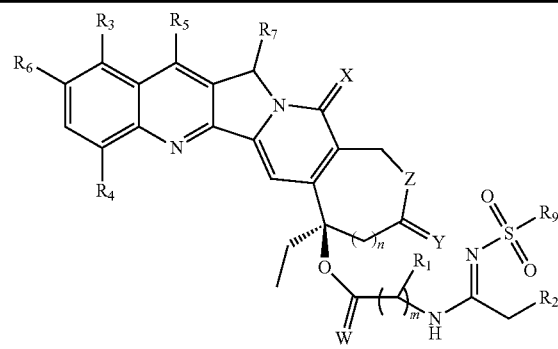

Y is O, W is O, Z is O, and n is 0.

| Compound | $R_3$ | $R_6$ | $R_4$ | $R_5$ | $R_7$ | $R_2$ | $R_9$ | $R_1$ | X | m |
|---|---|---|---|---|---|---|---|---|---|---|
| | H | H | H | $CH_3CH_2$ | H | 4-methoxyphenyl | 4-methylphenyl | $CH_3$ | O | 1 |
| | H | H | H | $CH_3CH_2$ | H | phenyl | 4-methylphenyl | $CH_3$ | O | 1 |
| Wept-03 | H | H | H | $CH_3CH_2$ | H | 4-methoxyphenyl | 4-methylphenyl | H | O | 1 |
| | H | H | H | H | H | 4-methoxyphenyl | $CH_3$ | H | O | 1 |
| | H | H | H | $CH_3CH_2$ | H | phenyl | 4-methylphenyl | H | O | 1 |
| | H | H | H | $CH_3CH_2$ | H | 4-methoxyphenyl | $CH_3$ | $CH_3$ | O | 1 |
| | H | H | H | $CH_3CH_2$ | H | 4-methoxyphenyl | $CH_3$ | H | O | 1 |
| | H | H | H | H | H | 4-chlorophenyl | 4-methylphenyl | H | O | 1 |
| | H | H | H | $CH_3CH_2$ | H | 4-chlorophenyl | 4-methylphenyl | $CH_3$ | O | 1 |
| | H | H | H | H | H | 4-methoxyphenyl | 4-methylphenyl | $CH_3$ | S | 1 |
| | H | H | H | H | H | 4-methoxyphenyl | 4-methylphenyl | H | S | 1 |

TABLE 5-continued

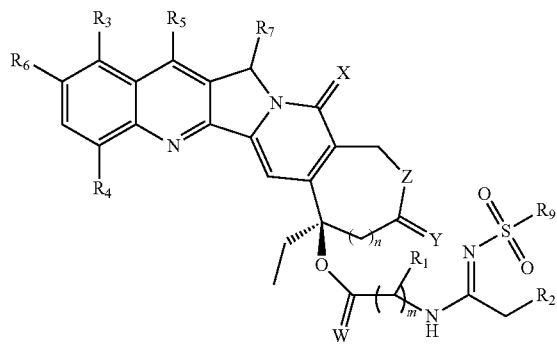

Y is O, W is O, Z is O, and n is 0.

| Compound | R₃ | R₆ | R₄ | R₅ | R₇ | R₂ | R₉ | R₁ | X | m |
|---|---|---|---|---|---|---|---|---|---|---|
| | NO₂ | H | H | H | H | phenyl | 4-methylphenyl | H | O | 1 |
| | NO₂ | H | H | H | H | 4-methoxyphenyl | 4-methylphenyl | H | O | 1 |
| | H | H | NO₂ | H | H | 4-methoxyphenyl | 4-methylphenyl | H | O | 1 |
| | H | H | H | H | H | 4-methoxyphenyl | 4-fluorophenyl | H | O | 1 |
| | H | H | H | H | H | 4-methoxyphenyl | 4-chlorophenyl | H | O | 1 |
| | H | H | H | H | H | 4-methoxyphenyl | 4-nitrophenyl | H | O | 1 |
| | H | H | H | H | H | 4-methylphenyl | 4-methylphenyl | H | O | 1 |
| | H | H | H | H | H | 4-methoxyphenyl | pyridin-3-yl | H | O | 1 |
| | H | H | H | H | H | 4-methoxyphenyl | naphthalen-1-yl | H | O | 1 |
| | H | H | H | H | H | 4-methoxyphenyl | N,N-dimethylamino | H | O | 1 |

TABLE 5-continued

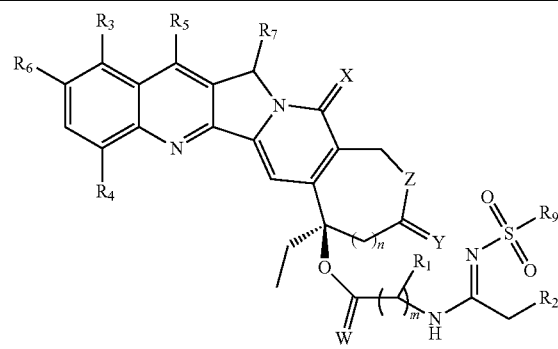

Y is O, W is O, Z is O, and n is 0.

| Compound | R3 | R6 | R4 | R5 | R7 | R2 | R9 | R1 | X | m |
|---|---|---|---|---|---|---|---|---|---|---|
| | H | H | H | H | CH3O | 4-methoxyphenyl | 4-methylphenyl | H | O | 1 |
| | H | H | H | H | H | 4-methoxyphenyl | 4-methylphenyl | H | O | 1 |
| | H | H | H | H | H | Si(CH3)3 | 4-methylphenyl | H | O | 1 |
| | H | H | H | H | H | 4-methoxyphenyl | thien-3-yl | H | O | 1 |
| | H | H | H | H | H | 4-methoxyphenyl | n-pentyl | H | O | 1 |
| | H | H | H | H | H | 4-methoxyphenyl | 4-methoxyphenyl | H | O | 1 |
| | H | H | H | H | H | 4-methoxyphenyl | ethyl | H | O | 1 |
| | H | H | H | H | H | 4-methoxyphenyl | 4-methylphenyl | H | O | 2 |
| | H | H | H | H | H | 4-methoxyphenyl | 4-methylphenyl | H | O | 3 |
| | H | H | H | H | H | 4-methoxyphenyl | 4-methylphenyl | H | O | 4 |

TABLE 5-continued

Y is O, W is O, Z is O, and n is 0.

| Compound | R₃ | R₆ | R₄ | R₅ | R₇ | R₂ | R₉ | R₁ | X | m |
|---|---|---|---|---|---|---|---|---|---|---|
| Wcpt-37 | H | OH | H | CH₃CH₂ | H | 4-methoxyphenyl | phenyl | H | O | 1 |
|  | H | OH | H | H | H | 4-methoxyphenyl | phenyl | H | O | 1 |
| Wcpt-39 | piperidin-4-yl piperidine-1-carboxyloxy | H | H | CH₃CH₂ | H | 4-methoxyphenyl | phenyl | H | O | 1 |
|  | methyl phosphate | H | H | CH₃CH₂ | H | 4-methoxyphenyl | phenyl | H | O | 1 |
| #9 | 4-(2-(4-methylpiperazin-1-yl)ethyl) | OH | H | H | H | 4-methoxyphenyl | phenyl | H | O | 1 |
| #10 | H | H | H | H | CH₃ | 4-methoxyphenyl | phenyl | H | O | 1 |
| #11 | H | H | H | H | H | 4-fluorophenyl | phenyl | H | O | 1 |

TABLE 6

| Compound | MDA-MB-468 (Breast cancer) | SKOV3 (Ovary cancer) | HCT 116 (Colon cancer) | A549 (Lung cancer) |
|---|---|---|---|---|
| 9a | 0.02285 ± 0.00297 μM | 0.01715 ± 0.00227 μM | 0.04613 ± 0.00174 μM | 0.08028 ± 0.00613 μM |
| Wcpt-37 | 0.00754 ± 0.00407 μM | 0.01163 ± 0.00408 μM | 0.05575 ± 0.00205 μM | 0.12055 ± 0.01578 μM |
| Wcpt-39 | 6.64094 ± 0.49707 μM | 4.37779 ± 0.67420 μM | 12.5119 ± 0.44525 μM | 30.7414 ± 2.12136 μM |
| #9 | 0.87139 ± 0.04494 μM | 1.69615 ± 0.27861 μM | 0.4577 ± 0.04633 μM | 13.1775 ± 1.09263 μM |
| #10 | 1.64684 ± 0.09085 μM | 0.13169 ± 0.02421 μM | 2.08505 ± 0.09615 μM | 2.80858 ± 0.41639 μM |
| #11 | 0.04971 ± 0.00653 μM | 0.03105 ± 0.00605 μM | 0.07187 ± 0.00259 μM | 0.12293 ± 0.00910 μM |
| Wcpt-03 | 0.01772 ± 0.00320 μM | 0.00808 ± 0.00167 μM | 0.20787 ± 0.00479 μM | 0.04835 ± 0.00172 μM |

Compound Wcpt-37

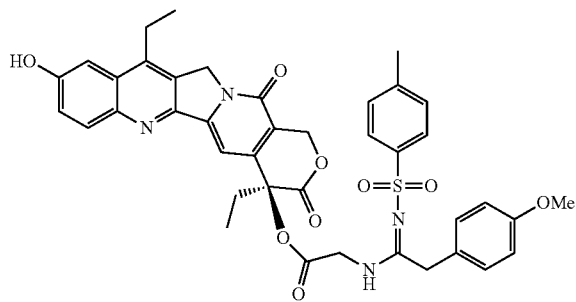 [SMILES: CCc1c2c(nc3ccc(O)cc13)-c1cc3c(c(=O)n1C2)COC(=O)[C@@]3(CC)OC(=O)CNC(Cc1ccc(OC)cc1)=NS(=O)(=O)c1ccc(C)cc1]

Compound Wcpt-37. Yield 50%; $^1$H NMR (DMSO-d$_6$, 400 MHz) δ: 8.88-9.00 (m, 1H, NH), 8.00 (d, 1H, J=10.0 Hz, C12-H), 7.54 (d, 2H, J=8.0 Hz, Ph-H), 7.40 (m, 2H, C11-H, C9-H), 7.18 (d, 2H, J=8.4 Hz, Ph-H), 7.03 (d, 2H, J=7.6 Hz, Ph-H), 7.00 (s, 1H, C14-H), 6.77 (d, 1H, J=8.4 Hz, Ph-H), 5.76 (s, 1H, C10-OH), 5.50 (s, 2H, C17-H), 5.29 (s, 2H, C5-H), 4.35 (dd, 1H, J=5.6, 18.0 Hz, C23-H), 4.24 (dd, 1H, J=5.6, 17.2 Hz, C23-H), 4.01 (s, 2H, C30-H), 3.66 (s, 3H, p-CH$_3$OPh), 3.11 (m, 2H, C7-CH$_2$CH$_3$), 2.21 (s, 3H, Ts-CH$_3$), 2.09-2.10 (m, 2H, C18-H), 1.29 (d, 3H, J=7.2 Hz, C7-CH$_2$CH$_3$), 0.84 (t, 3H, J=7.2 Hz, C19-H); MS-ESI m/z: 751.5 [M+H]$^+$.

Compound Wcpt-39

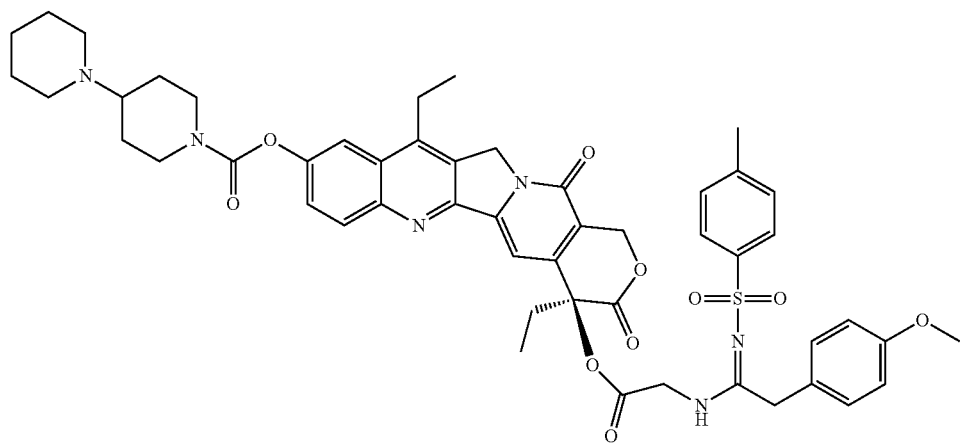 [SMILES: CCc1c2c(nc3ccc(OC(=O)N4CCC(N5CCCCC5)CC4)cc13)-c1cc3c(c(=O)n1C2)COC(=O)[C@@]3(CC)OC(=O)CNC(Cc1ccc(OC)cc1)=NS(=O)(=O)c1ccc(C)cc1]

Compound Wcpt-39. Yield 51%; $^1$H NMR (DMSO-d$_6$, 400 MHz) δ: 8.93 (s, 1H, NH), 8.14 (d, 1H, J=9.2 Hz, C12-H), 7.98 (s, 1H, C9-H), 7.65 (d, 1H, J=9.2 Hz, C11-H), 7.51 (d, 2H, J=8.0 Hz, Ph-H), 7.18 (d, 2H, J=8.4 Hz, Ph-H), 7.07 (s, 1H, C14-H), 6.98 (d, 2H, J=8.4 Hz, Ph-H), 6.76 (d, 2H, J=8.4 Hz, Ph-H), 5.52 (s, 2H, C17-H), 5.34 (s, 2H, C5-H), 4.19-4.39 (m, 4H, C7-CH$_2$, C23-H), 4.00 (s, 2H, C30-H), 3.65 (s, 3H, p-CH$_3$OPh-H), 3.08-3.20 (m, 4H, C1'-H, C1"-H), 2.92 (t, 1H, J=12.4 Hz, C3'-H), 2.74 (m, 6H, C7-CH$_2$CH$_3$, C4'-H, 4"-H), 2.40 (s, 3H, Ts-CH$_3$), 2.06-2.24 (m, 7H, C6'-H, C5'-H, C5"-H, C18-H), 2.05 (m, 4H, C4'-H, C4"-H), 1.71 (t, 3H, J=7.2 Hz, C7-CH$_2$CH$_3$), 0.84 (t, 3H, J=7.2 Hz, C19-H); MS-ESI m/z: 945.2 [M+H]$^+$.

Compound #9

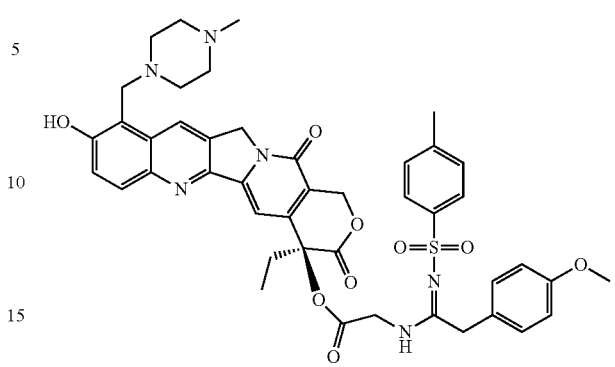

Compound #9 Yield 42%; $^1$H NMR (DMSO-d$_6$, 400 MHz) δ 8.92 (t, 1H, J=5.6 Hz, NH), 8.75 (s, 1H, C7-H), 7.95 (d, 1H, J=9.2 Hz, C12-H), 7.50 (d, 2H, J=8.0 Hz, Ph-H), 7.44 (d, 1H, J=9.2 Hz, C11-H), 7.18 (d, 2H, J=8.8 Hz, Ph-H), 6.97-7.03 (m, 3H, C14-H, Ph-H), 6.77 (d, 2H, J=8.4 Hz, Ph-H), 5.50 (s, 2H, C17-H), 5.23 (s, 2H, C5-H), 4.20-4.39 (m, 2H, C23), 4.04 (s, 2H, C30-H), 4.00 (s, 2H, 9-CH$_2$—), 3.68 (s, 3H, -PhOCH$_3$), 2.67-2.90 (m, 8H, piperazine-H), 2.37 (s, 3H, piperazine-CH$_3$), 2.20 (s, 3H, Ts-CH$_3$), 2.10-2.13 (m, 2H, C18-H), 0.84 (m, 3H, C19-H); MS-ESI m/z: 835.3 [M+H]$^+$.

Compound #10

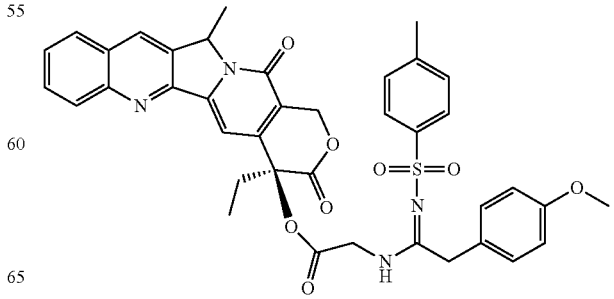

Compound #10. Yield 64%; $^1$H NMR (DMSO-d$_6$, 400 MHz) δ 8.91 (t, 1H, J=5.6 Hz, NH), 8.69 (s, 1H, C7-H), 8.10-8.15 (m, 2H, C9-H, C12-H), 7.83-7.84 (m, 1H, C11-H), 7.71 (t, 1H, J=7.6 Hz, C10-H), 7.49 (d, 2H, J=8.0 Hz, Ph-H), 7.17 (d, 2H, J=8.4 Hz, Ph-H), 7.10 (s, 1H, C14-H), 7.00-7.03 (m, 2H, Ph-H), 6.76 (d, 2H, J=8.8 Hz, Ph-H), 5.41-5.76 (m, 3H, C17-H, C5-H), 4.21-4.39 (m, 2H, C23), 4.00 (s, 2H, C30-H), 3.67 (s, 3H, -PhOCH$_3$), 2.20 (s, 3H, Ts-CH$_3$), 2.11-2.13 (m, 2H, C18-H), 1.83-1.87 (m, 3H, 5-CH$_3$), 0.85 (m, 3H, C19-H); MS-ESI m/z: 743.2 [M+Na]$^+$.

Compound #11

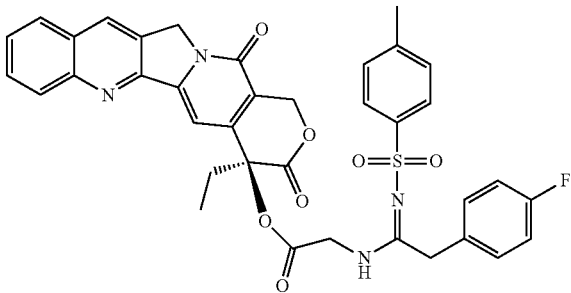

Compound #11. Yield 62%; $^1$H NMR (DMSO-d$_6$, 400 MHz) δ 9.10 (s, 0.5H, NH), 8.90 (s, 0.5H, NH), 8.69 (s, 1H, C7-H), 8.12-8.14 (m, 2H, C9-H, C12-H), 7.85 (t, 1H, J=7.6 Hz, C11-H), 7.71 (t, 1H, J=7.2 Hz, C10-H), 7.48-7.52 (m, 2H, Ph-H), 7.17-7.31 (m, 2H, Ph-H), 7.12 (s, 1H, C14-H), 7.02-7.06 (m, 3H, Ph-H), 6.76 (d, 1H, J=8.4 Hz, Ph-H), 5.52 (s, 2H, C17-H), 5.29 (s, 2H, C5-H), 4.21-4.39 (m, 2H, C23), 4.00 (s, 2H, C30-H), 2.20 (s, 3H, Ts-CH$_3$), 2.11-2.13 (m, 2H, C18-H), 0.85 (m, 3H, C19-H); MS-ESI m/z: 695.2 [M+H]+.

Compound #13

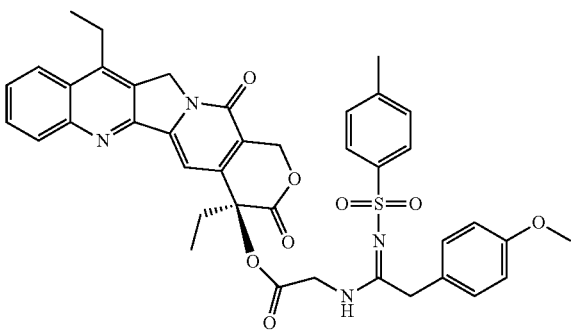

Compound #13. Yield 56%; $^1$H NMR (DMSO-d$_6$, 400 MHz) δ: 8.88 (t, 1H, J=5.8 Hz, NH), 8.28 (d, 1H, J=8.2 Hz, C9-H), 8.13 (d, 1H, J=7.8 Hz, C12-H), 7.83 (t, 1H, J=7.2 Hz, C11-H), 7.71 (t, 1H, J=7.2 Hz, C10-H), 7.52 (d, 2H, J=8.2 Hz, Ph-H), 7.18 (d, 2H, J=8.8 Hz, Ph-H), 7.08 (s, 1H, C14-H), 7.01 (d, 2H, J=8.0 Hz, Ph-H), 6.76 (d, 1H, J=8.8 Hz, Ph-H), 5.51 (s, 2H, C17-H), 5.32 (s, 2H, C5-H), 4.35 (dd, 1H, J=6.0, 18.0 Hz, C23-H), 4.28 (dd, 1H, J=6.0, 18.0 Hz, C23-H), 4.00 (s, 2H, C30-H), 3.64 (s, 3H, p-CH$_3$OPh), 3.22 (q, 2H, J=7.4 Hz, C7-CH$_2$CH$_3$), 2.19 (s, 3H, Ts-CH$_3$), 2.10-2.12 (m, 2H, C18-H), 1.30 (d, 3H, J=7.6 Hz, C7-CH$_2$CH$_3$), 0.84 (t, 3H, J=7.2 Hz, C19-H); MS-ESI m/z: 735.8 [M+H]$^+$.

REFERENCES (1) Wall, M. E.; Wani, M.; Cook, C. E.; Palmer K. H.; McPhail, A. T.; Sim, G. A. Plant antitumor agents. I. The isolation and structure of camptothecin, a novel alkaloidal leukemia and tumor inhibitor from *Camptotheca acuminata*. *J. Am. Chem. Soc.* 1966, 88, 3888-3890.

(2) Wang, H. K.; Morris-Natschke, S. L.; Lee, K. H. Antitumor agents 170. Recent advances in the discovery and development of topoisomerase inhibitors as antitumor agents. *Med. Res. Rev.* 1997, 17, 367-425, and literature cited therein.

(3) Oberlies, N. H.; Kroll, D. J. Camptothecin and taxol: historic achievements in natural products research. *J. Nat. Prod.* 2004, 67, 129-135.

(4) Hsiang, Y. H.; Hertzberg, R.; Hecht, S. M.; Liu, L. F. Camptothecin induces protein-linked DNA breaks via mammalian DNA topoisomerase I. *J. Biol. Chem.* 1985, 260, 14873-14878.

(5) Pommier, Y.; Kohlhagen, G. K.; Kohn, K. W.; Leteurtre, F.; Wani, M. C.; Wall, M. E. Interaction of an alkylating camptothecin derivative with a DNA base at topoisomerase I-DNA cleavage sites. *Proc. Natl. Acad. Sci. U.S.A.* 1995, 92, 8861-8865.

(6) Liew, S. T.; Yang, L. X. Design, synthesis and development of novel camptothecin drugs. *Curr. Pharm. Des.* 2008, 14, 1078-1097.

(7) Li, Q. Y.; Zu, Y. G.; Shi, R. Z.; Yao, L. P. Review camptothecin: current perspectives. *Curr. Med. Chem.* 2006, 13, 2021-2039.

(8) Rahier, N. J.; Thomas, C. J.; Hecht, S. M. Camptothecin and its analogs. In *Anticancer Agents from Natural Products*. Cragg, G. M.; Kingston, D. G. I.; Newman, D. J. (Eds.), CRC Press: New York, 2012, 5-21, and literature cited therein.

(9) Adams, D. J. The impact of tumor physiology on camptothecin-based drug development. *Curr. Med. Chem.: Anti-Cancer Agents* 2005, 5, 1-13.

(10) Tobin, P. J.; Rivory, L. P. Camptothecins and key lessons in drug design. *Drug Design Reviews—Online* 2004, 1, 341-346.

(11) Hatefi, A.; Amsden, B. Camptothecin delivery methods. *Pharm. Res.* 2002, 19, 1389-1399.

(12) Onishi, H.; Machida, Y. Macromolecular and nanotechnological modification of camptothecin and its analogs to improve the efficacy. *Curr. Drug Discovery Technol.* 2005, 2, 169-183.

(13) Sirikantaramas, S.; Asano, T.; Sudo, H.; Yamazaki, M.; Saito, K. Camptothecin: therapeutic potential and biotechnology. *Curr. Pharm. Biotechnol.* 2007, 8, 196-202.

(14) Fassberg, J.; Stella, V. J. A kinetic and mechanistic study of the hydrolysis of camptothecin and some analogues. *J. Pharm. Sci.* 1992, 81, 676-684.

(15) Zhao, H.; Lee, C.; Sai, P.; Choe, Y. H.; Boro, M.; Pendri, A.; Guan, S.; Greenwald, R. B. 20-O-Acylcamptothecin derivatives: evidence for lactone stabilization. *J. Org. Chem.* 2000, 65, 4601-4606.

(16) Liu, Y. Q.; Tian, X.; Yang, L.; Zhan, Z. C. First synthesis of novel spin-labeled derivatives of camptothecin as potential antineoplastic agents. *Eur. J. Med. Chem.* 2008, 43, 2610-2614.

(17) Yang, L.; Zhao, C. Y.; Liu, Y. Q. Synthesis and biological evaluation of novel conjugates of camptothecin and 5-flurouracil as cytotoxic agents. *J. Braz. Chem. Soc.* 2011, 22, 308-318.

(18) Yang, L. X.; Pan, X.; Wang, H. J. Novel camptothecin derivatives. Part 1: oxyalkanoic acid esters of camptothecin and their in vitro and in vivo antitumor activity. *Bioorg. Med. Chem. Lett.* 2002, 12, 1241-1244.

(19) Cao, Z.; Harris, N.; Kozielski, A.; Vardeman, D.; Stehlin, J S.; Giovanella, B. Alkyl esters of camptothecin and 9-nitrocamptothecin: synthesis, in vitro pharmacokinetics, toxicity, and antitumor activity. *J. Med. Chem.* 1998, 41, 31-37.

(20) De Groot, F. M. H.; Busscher, G. F.; Aben, R. W. M.; Scheeren, H. W. Novel 20-carbonate linked prodrugs of camptothecin and 9-aminocamptothecin designed for activation by tumour-associated plasmin. *Bioorg. Med. Chem. Lett.* 2002, 12, 2371-2376.

(21) Lerchen, H. G.; Baumgarten, J.; von dem Bruch, K.; Lehmann, T. E.; Sperzel, M.; Kempka, G.; Fiebig, H. H. Design and optimization of 20-O-linked camptothecin glycoconjugates as anticancer agents. *J. Med. Chem.* 2001, 44, 4186-4195.

(22) Greenhill, J. V.; Lue, P. Amidines and guanidines in medicinal chemistry. *Prog. Med. Chem.* 1993, 30, 203-326.

(23) Rauws, T. R. M.; Maes, B. U. W. Transition metal-catalyzed N-arylations of amidines and guanidines. *Chem. Soc. Rev.* 2012, 41, 2463-2497

(24) Sondhi, S. M.; Dinodia, M.; Jain, S.; Kumar, A. Synthesis of biologically active N-methyl derivatives of amidines and cyclized five-membered products of amidines with oxalyl chloride. *Eur. J. Med. Chem.* 2008, 43, 2824-2830.

(25) Rahmathullah, S. M.; Hall, J. E.; Bender, B. C.; McCurdy, D. R.; Tidwell, R. R.; Boykin, D. W. Prodrugs for amidines: synthesis and anti-*pneumocystis carinii* activity of carbamates of 2,5-bis(4-amidinophenyl)furan. *J. Med. Chem.* 1999, 42, 3994-4000.

(26) Casini, A.; Scozzafava, A.; Mastrolorenzo, A.; Supuran, C. T. Sulfonamides and sulfonylated derivatives as anticancer agents. *Curr. Cancer Drug Targ.* 2002, 2, 55-75.

(27) Nishino, R.; Ikeda, K.; Hayakawa, T.; Takahashi, T.; Suzuki, T.; Sato, M. Syntheses of 2-deoxy-2,3-didehydro-N-acetylneuraminic acid analogues modified by N-sulfonylamidino groups at the C-4 position and biological evaluation as inhibitors of human parainfluenza virus type 1. *Bioorg. Med. Chem.* 2011, 19, 2418-2427.

(28) Takasuna K.; Kasai, Y.; Kitano, Y.; Mori, K.; Kobayashi, R.; Hagiwara, T.; Kakihata K.; Hirohashi, M.; Nomura, M.; Nagai, E. Protective effects of kampo medicine and baicalin against intestinal toxicity of a new anticancer camptothecin derivative, irinotecan hydrochloride (CPT-11), in rats. *Jpn. J. Cancer Res.* 1995, 86, 978-984.

(29) Bae, I.; Han, H.; Chang, S. Highly efficient one-pot synthesis of N-sulfonylamidines by Cu-catalyzed three-component coupling of sulfonyl azide, alkyne, and amine. *J. Am. Chem. Soc.* 2005, 127, 2038-2039.

(30) Skehan, P.; Storeng, R.; Scudiero, D.; Monks, A.; McMahon, J.; Vistica, D.; Warren, J. T.; Bokesch, H.; Kenney, S.; Boyd, M. R. New colorimetric cytotoxicity assay for anticancer-drug screening. *J. Natl. Cancer Inst.* 1990, 82, 1107-1112.

(31) Li, T. K.; Liu, L. F. Tumor cell death induced by topoisomerase-targeting drugs. *Annu. Rev. Pharmacol. Toxicol.* 2001, 41, 53-77.

(32) Desai, S. D.; Zhang, H.; Rodriguez-Bauman, A.; Yang, J. M.; Wu, X.; Gounder, M. K.; Rubin, E. H.; Liu, L. F. Transcription-dependent degradation of topoisomerase I-DNA covalent complexes. *Mol. Cell. Biol.* 2003, 23, 2341-2350.

(33) Takemura, H.; Rao, V. A.; Sordet, O.; Furuta, T.; Miao, Z. H.; Meng, L.; Zhang, H.; Pommier, Y. Defective Mre11-dependent activation of Chk2 by ataxia telangiectasia mutated in colorectal carcinoma cells in response to replication-dependent DNA double strand breaks. *J. Biol. Chem.* 2006, 281, 30814-30823.

(34) Kastan, M. B.; Bartek, J. Cell-cycle checkpoints and cancer. *Nature* 2004, 432, 316-323.

(35) Kunimoto, T.; Nitta, K.; Tanaka, T.; Uehara, N.; Baba, H.; Takeuchi, M.; Yokokura, T.; Sawada, S.; Miyasaka, T.; Mutai, M. Antitumor activity of 7-ethyl-10-[4-(1-piperidino)-1-piperidino]carbonyloxy-camptothecin, a novel water-soluble derivative of camptothecin, against murine tumors. *Cancer Res.,* 1987, 47, 5944-5947

(36) Shackelford, C.; Long, G.; Wolf, J.; Okerberg, C.; Herbert, R. Qualitative and quantitative analysis of non-neoplastic lesions in toxicology studies. *Toxicol. Pathol.,* 2002, 30, 93-96.

The invention claimed is:

1. A compound having the following structure:

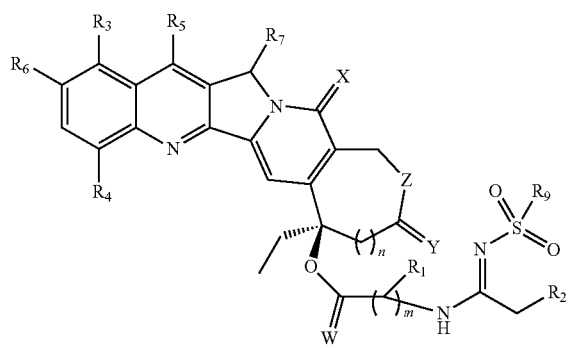

wherein $R_1$ is H, C1-C6 alkyl, or phenyl C1-C3 alkyl;

$R_2$ is hydroxyl C1-C6 alkyl, $(CH_3)_kH_{3-k}Si$, phenyl, C1-C3 alkyl phenyl, C1-C3 alkoxyl phenyl, fluorophenyl, chlorophenyl, bromophenyl, $(CH_2)_j$—O—$(CH_2)_i$—$R_{11}$, wherein k is 0, 1, 2 or 3; j is 1-5; i is 0-5; and $R_{11}$ is

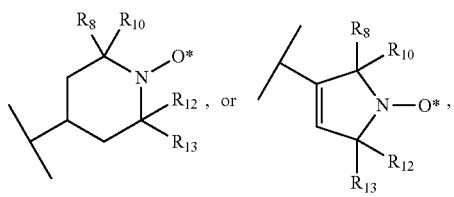

wherein $R_8$, $R_{10}$, $R_{12}$, and $R_{13}$ independently are H or C1-C6 alkyl;

$R_3$ is H, $NO_2$,

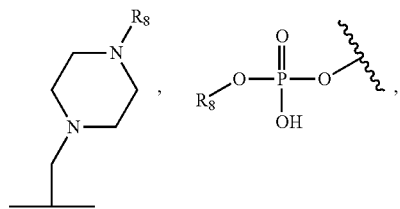

-continued

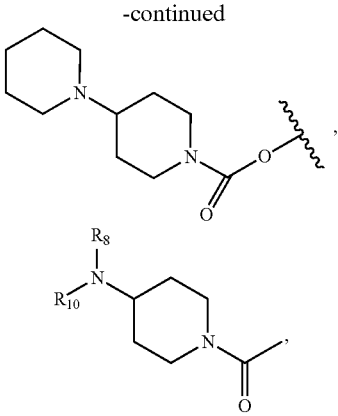

wherein $R_8$ and $R_{10}$ are defined as above;
$R_4$ is H or $NO_2$;
$R_5$ is H, C1-C6 alkyl,

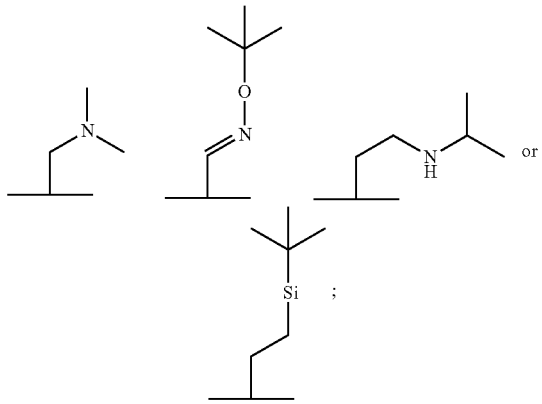

$R_6$ is H, OH, or

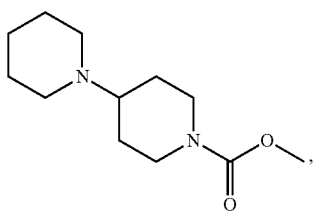 [SMILES: COC(=O)N1CCC(N2CCCCC2)CC1]

$R_7$ is H, C1-C6 alkyl or C1-C6 alkoxyl; and
$R_9$ is H, C1-C6 alkyl, phenyl, C1-C3 alkyl phenyl, C1-C3 alkoxyl phenyl, fluorophenyl, chlorophenyl, bromophenyl, pyridyl, naphthyl, furyl, thienyl, pyrrolyl,

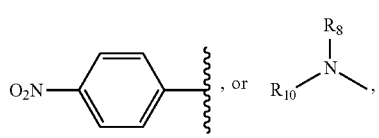

wherein $R_8$ and $R_{10}$ independently are H or C1-C6 alkyl;
n is 0-3;
m is 1-5;
X is O or S;
Y is O;
Z is O; and
W is O.

2. The compound of claim 1, wherein $R_3$, $R_4$, $R_5$, $R_6$ and $R_7$ are all H, n is 0, m is 1, and X is O.

3. The compound of claim 2, wherein $R_9$ is C1-C6 alkyl, C1-C3 alkyl phenyl, C1-C3 alkoxyl phenyl, fluorophenyl, chlorophenyl, or

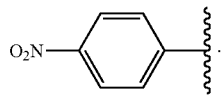 [SMILES: *c1ccc([N+](=O)[O-])cc1]

4. The compound of claim 3, wherein $R_2$ is hydroxyl C1-C6 alkyl, phenyl, C1-C3 alkoxyl phenyl, or $(CH_2)_j$—O—$(CH_2)_i$—$R_{11}$, wherein j is 1; i is 0 or 1; and $R_{11}$ is

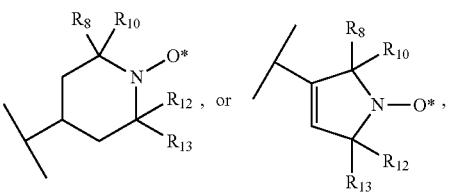

wherein $R_8$, $R_{10}$, $R_{12}$, and $R_{13}$ are all methyl.

5. The compound of claim 4, wherein $R_1$ is H, C1-C6 alkyl, or phenylmethyl.

6. The compound of claim 5, wherein $R_2$ is p-methoxyphenyl.

7. The compound of claim 5, wherein $R_2$ is $(CH_2)_j$—O—$(CH_2)_i$—$R_{11}$, wherein j is 1; i is 0 or 1; and $R_{11}$ is

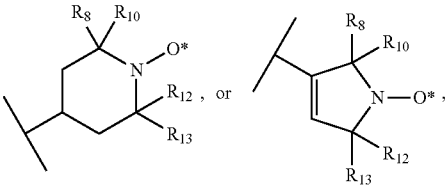

wherein $R_8$, $R_{10}$, $R_{12}$, and $R_{13}$ are all methyl.

8. The compound of claim 1, wherein $R_2$ is p-methoxyphenyl or p-fluorophenyl, $R_1$ and $R_4$ are both H, $R_9$ is p-methylphenyl, n is 0, m is 1, and X is O.

9. The compound of claim 8, wherein $R_5$ is $CH_3CH_2$, $R_6$ is H or OH, $R_7$ is H, $R_2$ is p-methoxyphenyl, and $R_3$ is H.

10. The compound of claim 8, wherein $R_5$ is $CH_3CH_2$, $R_6$ is H, $R_7$ is H, $R_2$ is p-methoxyphenyl, and $R_3$ is

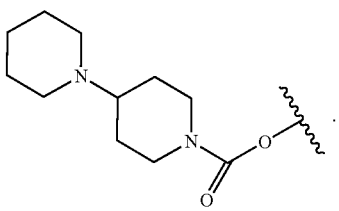 [SMILES: *OC(=O)N1CCC(N2CCCCC2)CC1 ; "."]

11. The compound of claim 8, wherein $R_5$ and $R_7$ are both H, $R_6$ is OH, $R_2$ is p-methoxyphenyl, and $R_3$ is

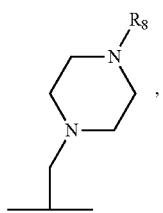

wherein $R_8$ is methyl.

12. The compound of claim 8, wherein $R_3$, $R_5$ and $R_6$ are all H, $R_7$ is methyl, $R_2$ is p-methoxyphenyl.

13. The compound of claim 8, wherein $R_3$, $R_5$, $R_6$ and $R_7$ are all H, $R_2$ is p-fluorophenyl.

14. A method for inhibiting growth of cancer cells comprising administering a compound as set forth in claim 1 or a pharmaceutically acceptable salt thereof, to a subject suffering cancer in need of said inhibition,
wherein the cancer is colon cancer, nasopharyngeal cancer, lung cancer, breast cancer, prostate cancer or ovary cancer.

15. The method of claim 14, wherein $R_3$, $R_4$, $R_5$, $R_6$ and $R_7$ are all H, n is 0, m is 1, and X is O.

16. The method of claim 15, wherein $R_9$ is C1-C6 alkyl, C1-C3 alkyl phenyl, C1-C3 alkoxyl phenyl, fluorophenyl, chlorophenyl, or

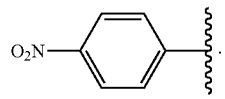

17. The method of claim 16, wherein $R_2$ is hydroxyl C1-C6 alkyl, phenyl, C1-C3 alkoxyl phenyl, or $(CH_2)_j$—O—$(CH_2)_i$—$R_{11}$, wherein j is 1; i is 0 or 1; and $R_{11}$ is

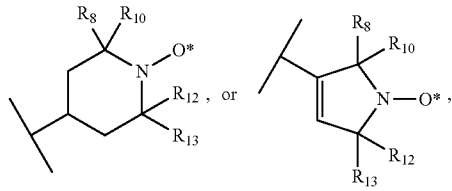

wherein $R_8$, $R_{10}$, $R_{12}$, and $R_{13}$ are all methyl.

18. The method of claim 17, wherein $R_1$ is H, C1-C6 alkyl, or phenylmethyl.

19. The method of claim 18, wherein $R_2$ is p-methoxyphenyl.

20. The method of claim 18, wherein $R_2$ is $(CH_2)_j$—O—$(CH_2)_i$—$R_{11}$, wherein j is 1; i is 0 or 1; and $R_{11}$ is

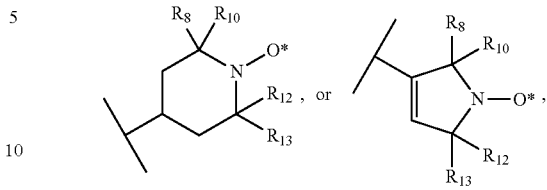

wherein $R_8$, $R_{10}$, $R_{12}$, and $R_{13}$ are all methyl.

21. The method of claim 14, wherein $R_2$ is p-methoxyphenyl or p-fluorophenyl, $R_1$ and $R_4$ are both H, $R_9$ is p-methylphenyl, n is 0, m is 1, and X is O.

22. The method of claim 21, wherein $R_5$ is $CH_3CH_2$, $R_6$ is H or OH, $R_7$ is H, $R_2$ is p-methoxyphenyl, and $R_3$ is H.

23. The method of claim 21, wherein $R_5$ is $CH_3CH_2$, $R_6$ is H, $R_7$ is H, $R_2$ is p-methoxyphenyl, and $R_3$ is

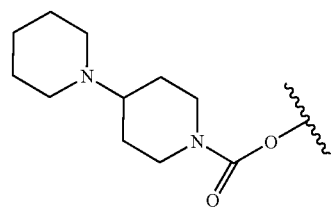

24. The method of claim 21, wherein $R_5$ and $R_7$ are both H, $R_6$ is OH, $R_2$ is p-methoxyphenyl, and $R_3$ is

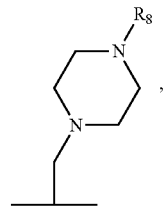

wherein $R_8$ is methyl.

25. The method of claim 21, wherein $R_3$, $R_5$ and $R_6$ are all H, $R_7$ is methyl, $R_2$ is p-methoxyphenyl.

26. The method of claim 21, wherein $R_3$, $R_5$, $R_6$ and $R_7$ are all H, $R_2$ is p-fluorophenyl.

* * * * *